US006658396B1

(12) United States Patent
Tang et al.

(10) Patent No.: US 6,658,396 B1
(45) Date of Patent: Dec. 2, 2003

(54) NEURAL NETWORK DRUG DOSAGE ESTIMATION

(76) Inventors: Sharon S. Tang, 4428 Maryland St., San Diego, CA (US) 92116; Cornelius Diamond, 4540 Georgia, San Diego, CA (US) 92116; Scott Arouh, 9344 Redwood Dr. Apt. H, San Diego, CA (US) 92037

( * ) Notice: Subject to any disclaimer, the term of this patent is extended or adjusted under 35 U.S.C. 154(b) by 0 days.

(21) Appl. No.: 09/451,249

(22) Filed: Nov. 29, 1999

(51) Int. Cl.[7] .................................................. G06N 3/02
(52) U.S. Cl. .......................... 706/17; 600/300; 600/544
(58) Field of Search ............................ 706/17; 600/300, 600/544

(56) References Cited

U.S. PATENT DOCUMENTS 5,775,330 A  *  7/1998  Kangas et al. ............... 600/544
5,860,917 A  *  1/1999  Comanor ..................... 600/300

OTHER PUBLICATIONS

Valafar, H.; Valafar, F., Prediction of a patient's response to a specific drug treatment using artificial neural networks, Neural Networks, 1999. IJCNN '99. International Joint Conference on, vol.: 5, Jul. 10–16, 1999, pp.: 3694–3697 vol. 5.*

Shadmehr, R.; D'Argenio, D.Z., Connectionist modeling vs. Bayesian procedures for sparse data pharmacokinetic parameter estimation, Engineering in Medicine and Biology Society, 1989. Images of the Twenty–First Century., Proceedings of the Annual Internati.*

Solaiman, B.; Picart, D., Neural networks modelling of biochemical reactions, Neural Networks, 1994. IEEE World Congress on Computational Intelligence., 1994 IEEE International Conference on, vol.: 5, Jun. 27–Jul. 2, 1994, pp.: 3348–3351 vol. 5.*

(List continued on next page.)

Primary Examiner—Willbert L. Starks, Jr.
(74) Attorney, Agent, or Firm—Fuess & Davidenas

(57) ABSTRACT

Neural networks are constructed (programmed), trained on historical data, and used to predict any of (1) optimal patient dosage of a single drug, (2) optimal patient dosage of one drug in respect of the patient's concurrent usage of another drug, (3a) optimal patient drug dosage in respect of diverse patient characteristics, (3b) sensitivity of recommended patient drug dosage to the patient characteristics, (4a) expected outcome versus patient drug dosage, (4b) sensitivity of the expected outcome to variant drug dosage(s), (5) expected outcome(s) from drug dosage(s) other than the projected optimal dosage. Both human and economic costs of both optimal and sub-optimal drug therapies may be extrapolated from the exercise of various optimized and trained neural networks. Heretofore little recognized sensitivities—such as, for example, patient race in the administration of psychotropic drugs—are made manifest. Individual prescribing physicians employing deviant patterns of drug therapy may be recognized. Although not intended to prescribe drugs, nor even to set prescription drug dosage, the neural networks are very sophisticated and authoritative "helps" to physicians, and to physician reviewers, in answering "what if" questions.

16 Claims, 20 Drawing Sheets

OTHER PUBLICATIONS

Linkens, D.A.; Shieh, J.S.; Peacock, J.E., SADAP: a simulator for hierarchical fuzzy control of depth of anaesthesia, Fuzzy Information Processing Society Biannual Conference, 1994. Industrial Fuzzy Control and Intelligent Systems Conference, and the NASA.*

Ashraf, S.A.; Khan, M.R.; Khan, S.A., Long term efficacy of Enalapiril using artificial neural network, Engineering in Medicine and Biology Society, 1996 and 14th Conference of the Biomedical Engineering Society of India. An International Meeting, Proceed.*

Conway, J.Y.; Polycarpou, M.M., Using adaptive networks to model and control drug delivery, IEEE Expert [see also IEEE Intelligent Systems], vol.: 11 Issue: 2, Apr. 1996 pp.: 31–37.*

Lada, P.; Brier, M.E.; Zurada, J.M., Therapeutic drug closing prediction using adaptive models and artificial neural networks, Neural Networks, 1999. IJCNN '99. International Joint Conference on, vol.: 5, Jul. 10–16, 1999, pp.: 3669–3673 vol. 5.*

* cited by examiner

Figure 6

| Darwinian Evolutionary Theory | Genetic Algorithms |
|---|---|
| Natural selection with an evolving fitness measure | Selection based on superimposed fixed fitness measure |
| Adaptation to changing environments | Optimization of fitness under stable environments |
| Complex stochastic genotype-to-phenotype mapping | Relatively simple deterministic genotype-to-phenotype mapping |
| Relatively low mutation rate | Relatively high mutation rate |
| Extreme high level of epistasis | Only perform well on problems with medium level epistasis |
| Competition between organisms for a common source | No competition between individuals |
| Baldwin effect: change in fitness function due to individual learning | Sometimes local learning but no change in fitness function |

NEURAL NETWORK DRUG DOSAGE ESTIMATION

BACKGROUND OF THE INVENTION

1. Field of the Invention

The present invention generally concerns the construction, training and use of neural networks for the optimization of the administration of drugs (and, for the invention, drug equivalents such as food and exercise) in respect of patient characteristics.

The present invention particularly concerns the construction, training and use of neural networks to better recognize any of (1) optimal patient dosage of a single drug, (2) optimal patient dosage of one drug in respect of the patient's concurrent usage of another drug, (3a) optimal patient drug dosage in respect of patient characteristics, (3b) sensitivity of patient recommended drug dosage to patient characteristics, (4a) expected outcome versus patient drug dosage, (4b) sensitivity of expected outcome to drug dosage, (5) expected outcome(s) from drug dosage(s) other than projected optimal dosage, from which expected outcome(s) costs both human and economic may be separately predicted.

2. Description of the Prior Art

2.1 Drug Dosage Estimation by Drug Developers and Physician Practitioners

Many ailments exist in society for which no absolute cure exists. These aliments include, to name a few, certain types of cancers, certain types of immune deficiency diseases and certain types of mental disorders. Although society has not found an absolute cure for these and many other types of disease, the use of drugs has reduced the negative effect of these disorders.

Generally the developers of drugs have two goals. First, they try to alter the drug user's biochemistry to correct the physiological nature of the illness. Second, they try to reduce the drug's negative side effects on the user. To accomplish these goals, drug developers utilize time consuming and scientifically advanced methods. These expensive efforts yield an extremely high cost for many drugs.

Unfortunately, when these costly drugs are distributed they are usually accompanied by only a crude system for assisting a doctor in determining an appropriate drug dosage for a patient. For instance, the annually printed *Physician's Desk Reference* summarizes experimentally determined reasonable drug dosage ranges found in the research literature. These ranges are general. The same dosage range is given for all patients.

Other publications exist which provide general methods to assist a doctor in determining an appropriate dosage. These references and manuals are not, however, directed towards providing a precise dosage range to match a specific patient. Rather, they provide a broad range of dosages based on an averaging of characteristics over an entire population of patients. The correlations between distinguishing patient characteristics and actual required dosages are never obtained, even in the original research.

Faced with the task of minimizing side effects and maximizing drug performance, doctors sometimes refine the dosage they prescribe for a given individual by trial and error. This method suffers from a variety of deleterious consequences. During the period that it takes for trial and error to find an optimal drug dosage for a given patient, the patient may suffer from unnecessarily high levels of side effects or low or totally ineffective levels of relief. Furthermore, the process wastes drugs, because it either prescribes a greater amount of drug than is needed or prescribes such a small amount of drug that it does not produce the desired effect. The trial and error method also unduly increases the amount of time that the patient and doctor must consult.

2.2 The Need for Drug Dosage Optimization

The past few decades have produced research identifying numerous factors that influence the clinical effects of medication. Age, gender, ethnicity, weight, diagnosis and diet have all been found to influence both the pharmacokinetics and pharmacodynamics of drugs. As a result, it is now acknowledged that women, minorities, and the elderly often require considerably lower doses of some medications than their male Caucasian counterparts. Furthermore, it is possible that patient variables have potentially varying strengths of influence for each case, and each drug. For example, weight may be of greater importance than age for a Caucasian male while the converse may be true for an African American female. See Lawson, W. B. (1996). The art and science of psychopharmacotherapy of African Americans. *Mount Sinai Journal of Medicine*, 63, 301–305. See also Lin, K. M., Poland, R. E., Wan, Y., Smith, M. W., Strickland, T. L., & Mendoza, R. (1991). Pharmacokinetic and other related factors affecting psychotropic responses in Asians. *Psychopharmacology Bulletin*, 27, 427–439. See also Mendoza, R., Smith, M. W., Poland, R., Lin, K., Strickland, T. (!991). Ethnic psychopharmacology: The Hispanic and Native American perspective. *Psychopharmacology Bulletin*, 27, 449–461. See also Roberts, J., & Tumer, N. (1988). Pharmacodynamic basis for altered drug action in the elderly. *Clinical Geriatric Medicine*, 4, 127–149. See also Rosenblat, R., & Tang, S. W. (1987). Do Oriental psychiatric patients receive different dosages of psychotropic medication when compared with Occidentals? *Canadian Journal of Psychiatry*, 32, 270–274. See also Dawkins, K., & Potter, Z. (1991). Gender differences in pharmacokinetics and pharmacodynamics of psychotropics: Focus on women. *Psychopharmacology Bulletin*, 27, 417–426.

The large number of potentially interacting variables to consider, in addition to the wide therapeutic windows of many drugs (including psychotropic drugs) have resulted in prescribing practices that rely mainly upon trial-and-error and the experience of the prescribing clinician.

The compensation process can be quite lengthy while drug consumers experiment with varying dosages. New methods are needed to reduce the time to compensation for patients (including psychiatric patients), thus alleviating their suffering more quickly as well as reducing the cost of hospitalization. The optimization of drug dosages would also help avoid unnecessarily high dosages, reducing the severity of the many side effects that typically accompany such medications and increasing the likelihood of long-term compliance with the prescribed regimen.

For decades, researchers have recognized the need for finding new methods of accounting for inter-individual differences in drug response. See, for example, Smith, M., & Lin, K. M. (1996); A biological, environmental, and cultural basis for ethnic differences in treatment; In P. M. Kato, & T. Mann (Eds.), *Handbook of Diversity Issues in Health Psychology* (pp. 389–406); New York: Plenum Press; and also Lenert, L., Sheiner, L., & Blaschke, T. (1989). Improving drug dosing in hospitalized patients: automated modeling of pharmacokinetics for individualization of drug dosage regimens; *Computational Methods in Programs Biomedical,* 30, 169–176.

However, a practical solution to tailoring drug regimens has yet to be implemented on a widespread basis.

2.3 Existing Pharmacological Software

Pharmacological software currently in use attempts to provide guidelines for drug dosages, but most software programs merely access databases of information rather than compute drug dosages. At best, these databases rely upon existing research that groups subjects in a few gross categories (e.g., the elderly, or children), and they usually do not include information regarding such relevant characteristics as weight or ethnicity.

The few analytical software products that make use of computer algorithms base their recommendations primarily upon blood plasma concentrations of the drug of interest. See, for example, Tamayo, M., Fernandez de Gatta, M., Garcia, M., & Dominguez, G. (1992); Dosage optimization methods applied to imipramine and desipramine in enuresis treatment; *Journal of clinical pharmacy and therapeutics,* 17, 55–59; and also Lacarelle B., Pisano P., Gauthier T., Villard P. H., Guder F., Catalin J., & Durand A. (1994); Abbott PKS system: a new version for applied pharmacokinetics including Bayesian estimation; *International Journal of Biomedical Computing,* 36, 127–30.

Although these methods have met with some success in research, there are several major drawbacks to their implementation. The necessity for constant blood draws for each patient being monitored hinders their practicality in the clinical setting. Furthermore, the limitations of the algorithms used allow modeling of no more than a few select characteristics at a time, thus ignoring all others. Finally, the models inherently comprise a single algorithm.

However, various drugs have been demonstrated to exhibit quite different response curves. Most new methods use a Bayesian model, which allows for the incorporation of individual response characteristics. See, for example, Tamayo, et al., op. cit. and also Kaufmann G. R., Vozeh S., Wenk M., Haefeli, W. E. (1998). Safety and efficacy of a two-compartment Bayesian feedback program for therapeutic tobramycin monitoring in the daily clinical use and comparison with a non-Bayesian one-compartment model; *Therapeutic Drug Monitoring,* 20, 172–80. Even so, the user must first select one rigid modeling equation.

2.4 Present Use of Neural Networks in the Health Sciences

Recent research has begun to demonstrate that the flexibility of neural networks in trying a variety of algorithms reduces the margin of error in prediction of blood plasma levels. See Brier, M. E., & Aronoff, G. R. (1996); Application of neural networks to clinical pharmacology; *International Journal of Clinical Pharmacology and Therapeutics,* 34, 510–514.

The past two to three years have produced a proliferation of studies in the application of neural nets to clinical pharmacology. For example, neural networks are now being used to automate the regulation of anesthesia. See Huang, J. W., Lu, Y. Y., Nayak, A., Roy, R. J. (1999); Depth of anesthesia estimation and control; *IEEE Trans Biomedical Engineering,* 46, 71–81.

Neural networks are used to determine optimal insulin regimens. See Trajanoski, Z., & Wach, P. (1998); Neural predictive controller for insulin delivery using the subcutaneous route; *IEEE Trans Biomedical Engineering,* 45, 1122–1134; and also Ambrosiadou, B. V., Gogon, G., Maglaveras, N., Pappas, C. (1996); Decision support for insulin regime prescription based on a neural net approach; *Medical Information,* 21, 23–34.

Neural networks are even used to predict clinical response to other medications. See Brier, M. E., et. al., op. cit. and also Bourquin, J., Schmidli, H., van Hoogevest, P., Leuenberger, H. (1997); Application of artificial neural networks (ANN) in the development of solid dosage forms; *Pharmacology Development Technology,* 2, 111–21.

However, few, if any, prior art references consider the influence of ethnicity. And none known to the inventors envision the comprehensive neural network optimization that will seen to be the subject of the present invention.

The full potential of neural network applications in medicine has yet to be realized, but their growing popularity has resulted in more sophisticated methodology. For example, a genetic algorithm was used to reduce the number of variables required for the training of a neural net in the prediction of patient response to the drug Warfarin. See Narayanan, M. N., & Lucas, S. B. (1993); A genetic algorithm to improve a neural network to predict a patient's response to Warfarin; *Methods in Information Medicine,* 32, 55–58.

However, most current models used in research are dated and not as efficient as those yet to be publicized such as the preferred Levenberg-Marquardt technique used in the present invention, and explained in detail below. Furthermore, although genetic algorithms have recently been used in the neurocomputing field to optimize network architectures, these research techniques have yet to be translated to the medical community or to medical applications (as is the subject of the present invention).

2.4 Diet and Exercise Management

It will be seen that both diet and exercise can be considered equivalent to drugs for purposes of applying the present invention. Equivalently to the often existing uncertainties with which patient characteristics of age, sex, ethnicity, etc., correlate with optimal drug dosage, it is often uncertain as to how exercise and/or diet will affect individuals of certain characteristics as regards induced changes in weight and/or blood pressure. Equivalently to the often existing uncertainties regarding the effects to be expected from changing the dosage of a drug, it is often difficult to answer for an individual patient questions such as "How little to I have to eat for how long to lose 50 pounds?" or "How much weight must I lose to lower my blood pressure into a safe range?" The present invention will be seen to be useful in reducing uncertainties, and in answering questions, in the areas of diet and exercise management as well as drug dosage estimation.

SUMMARY OF THE INVENTION

The present invention contemplates making (i.e., programming), training (optimizing) and using neural networks (i) in order to estimate the optimal dosage of one or more drugs for a particular patient, as well as—likely equally or more importantly—(ii) to render better visible many factors concerning the proper dosage(s) of drugs (and drug equivalents, such as diet and exercise), and the sensitivity of both drug dosage(s) and therapeutic outcomes to these factors.

The neural-network-based, computerized, drug dosage estimator of the present invention combines a number of variables influencing drug response into a single empirical computer model that can be easily used to (i) refine prescribing practices (including on the individual patient level), as well as to (iii) generate future hypothesis testing regarding the underlying mechanisms of each component.

In simplest terms, the neural network drug dosage estimator of the present invention predicts optimal drug dosages for populations or individuals based on the multi-faceted characteristics of such populations or individuals. Because the drug dosage estimation model can be run for populations of various characteristics, it is clearly possible to quickly learn which population or patient characteristic(s) is (are) of greatest significance for each drug. For example, ethnicity is believed by the inventors to presently (circa 1999) be an underweighted factor in the prescription of many drugs, and especially psychotropic drugs.

Less clearly, it is possible to exercise the computerized neural network drug dosage estimator of the present invention to predict what will happen when a patient, or a patient population, is administered a drug dosage deviating from predicted optimal. For example, if an individual patient of certain characteristics does not exhibit desired therapeutic response at a certain (possibly even the predicted optimal) drug dosage level, then should the dosage be increased by 10%, or by 25%, or by 50%, or even by 100%? Exercise of the neural network drug dosage estimator of the present invention helps to definitively answer this question.

A drug dosage neural network of the present invention arguably presents a major innovation in pharmacology because it works, and works well. The drug dosage neural network does so work particularly because its architecture has been optimized (via competitive selection) relative to real-world historical clinical data. Still more particularly, the drug dosage neural network works and works well because its optimal neural net architecture is selected using an advanced technique—a genetic algorithm. Such neural networks as have heretofore been employed in the health sciences have not been optimized at all to the best knowledge of the inventors, and certainly not by use of a fast genetic algorithm.

1. Objectives of the Present Invention

The primary objective of the present invention is the realization of an algorithmically-based, computerized, accurate optimization of drug dosage, including psychotropic drug dosage, for an individual patient based on data regarding that individual patient. The computerized drug dosage estimator of the present invention is based on a neural network coupled with a genetic algorithm to map clinically determined stabilizing dosages of several drugs as a function of individual characteristics.

A neural net architecture especially suited to this problem, including a specific genetic algorithm to increase modeling accuracy, is taught within this specification. Greater accuracy and finer precision of drug dosage ranges, including psychotropic drug dosage ranges, are realizable by the simple-to-use, non-intrusive tool of the present invention employing a computer algorithm that accounts for the many variables that influence clinical drug response.

The practical effect of the present invention is to alleviate much of the guesswork in prescribing medication, particularly including psychotropic medication, and to thus reduce the number and severity of side effects, and/or sub-optimal or ineffective therapeutic effectiveness, unnecessarily suffered by an individual patient when the drug dosage prescribed for such patient is incorrect. The inventors project that the optimization of drug dosages accorded by the present invention will most greatly succor those populations that have historically been the most sensitive to medications: women, children, minority groups, and the elderly. However, the optimization of drug dosages accorded by the present invention will benefit us all by alleviating the tremendous wastage or drugs, and prolongation of illness, that results from the proscribing of drugs at a non-optimal levels, individual patient by individual patient.

2. Identifying (Selecting) and Training a Neural Network to Predict Drug Dosage

The computerized neural networks of the present invention are derived from, and are proven upon, actual historical patient data concerning the administration of, and results from, drug therapies. The neural networks are derived: they are not strictly dependent upon what their originator—a neural network architect—initially thinks to be the proper choice(s) of, and interplay between, patient factors in accordance with which drug dosages would presumptively best be prescribed. ("Patient factors" include things like (1) overt indications of (1a) age, (1b) gender, (1c) race, (1d) ethnicity, (1e) diet type, (1f) height, (1g) weight, and (1h) body surface area; (2) medical diagnostic indications of (2a) blood pressure, (2b) use of a drug other than the particular drug at the same time as use of the particular drug, (2c) fitness, (2d) peptide levels, and (2e) genetic predisposition to a particular disease; and (3) pharmacological indications of (3a) pharmacokinetic parameters and (3b) pharmacodynamic parameters.)

Instead, the neural networks are selected, or optimized, by and in a standard genetic selection algorithm. What is derived, after 5, or 10 or even 20 iterations is a single selected optimal neural network.

In accordance that the optimal neural network is selected by empirical historical patient data drug response data, this network may—and often does at the present state of advance in the medical arts for the precision administration of many drugs especially including psychotropic drugs—deliver optimal drug dosage results that may come as a great surprise to a physician prescriber of the drug, downplaying or ignoring factors that physicians have deemed important and elevating factors that were previously ignored, or perceived to be of lesser importance. For example, patient race and ethnicity turn out to be an unexpectedly important factors in the administration of psychotropic drugs. (It will be understood, however, that the present invention is not a drug dosage scheme for any particular drug, or class of drugs, but a methodology for determining optimal drug dosage.)

Simultaneously to being selected, the optimal neural network becomes trained on the historical patient data. (It may thus be said the optimal trained neural network is the one being selected.) This training may be, by way of example, in accordance with either the (i) Levenberg-Marquardt (L-M) or the (ii) back propagation methods of neural network optimization.

This (i) optimization (selection) and (ii) training of neural networks produces an optimized trained neural network—a programmed computer process—that is very effective to predict from patient characteristics an optimal therapeutic drug dosage.

For example, the inventors have found that optimized trained neural networks for predicting the optimal dosage(s) of psychotropic drugs show a large and unexpected dependence upon the patient's race and ethnicity. Therefore, and although patient factors like sex, age and weight might well be expected to be taken into consideration by a skilled prescribing physician, the neural network may, by its very existence, serve to highlight additional patient factors, such as race, that are suitably considered in prescribing drugs at an optimal level.

Under the laws of all States, a machine, even a computer-based neural network program, cannot prescribe drugs. The method, and the diverse optimized trained neural networks, of the present invention are used to support physician prescription of drugs. They do so by identifying and illuminating factors (mostly patient factors, but also cost factors) of relevance to drug therapy, and to optimized drug therapy. Accurate identification of these factors could potentially save millions of dollars in drugs prescribed and taken at levels to low to be effective, or at levels higher than are useful.

3. Building and Using Optimized Trained Neural Networks for Drug Dosage Sensitivity Analysis The present invention can also illuminate (ii) the sensitivity of therapeutic outcomes to these factors. One physician may modify his/her predilection for minimal dosages when he/she observes that exercise of an optimized neural network program for a Particular Patient not only indicates a higher recommended dosage, but predicts total pharmacological ineffectiveness at the level the physician desires to prescribe. Another physician may modify his/her predilection for potent dosages when he/she observes that exercise of an optimized neural network program for a Particular Patient not only indicates a lower recommended dosage, but predicts an avalanche of side effects at the level the physician desires to prescribe.

Even a neural network relating the dosage between two or more drugs taken concurrently by a single patient may be developed, optimized and trained, serving thereafter to predict the proper dosage of each drug in respect of the patient's concurrent consumption of the other.

For example, a neural network need not be exercised solely to predict optimal drug dosage when all other factors are known, and are supplied as inputs to the solution of the neural network. The network may instead be exercised to assess the sensitivity—in terms of expected therapeutic outcomes of a drug therapy for a particular patient—when drug dosage is varied. Consider, for example, a patient that is not responding as desired at drug dosage "X". This dosage "X' may have even been the dosage predicted optimal by the neural network; it matters not. The important thing is, the present dosage proving inadequate, should the dosage be increased to 1.5X? to 2X? to 3X? Suppose the neural network, when exercised with hypothetical drug dosages, shows a very sharp "onset of effectiveness" coupled with adverse side effects at "overdoses". This might mean that the attending physician might try and "ease into" the correct drug dosage level, initially increasing the drug dosage to, by way of example, only 1.5X.

For example, the sensitivity of drug dosage to a factor like patient weight can be examined. Suppose a patient performing satisfactorily on a drug at a conventional, predicted, optimal dosage level both (i) loses weight and (ii) commences to complain about drug side effects. Can the drug dosage safely be lowered while retaining therapeutic effectiveness? Some exercise of an appropriate neural network can provide insight into answering this question.

For example, the effect of one drug upon the recommended optimal dosage of another drug, and vice versa, may be examined with a drug interaction neural network in accordance with the present invention.

The neural networks of the present invention may be used as a sophisticated filter to isolate and examine the propensities and proclivities of drug-prescribing physicians. Does a physician frequently prescribe drugs at higher, or lower, dosages than a target optimal range? Does he or she routinely ignore sex and/or weight, giving the same drug dosages to small women as to large men? Or are the patterns of the drug-dispensing physician more subtle, such as a general practitioner who, while having never in his/her entire career made a recorded referral for high blood pressure in a patient less than fifty years of age, also has a personal map of drugs historically prescribed that is all but totally devoid of any anti-hypertensives whatsoever, showing only two prescriptions for reserpine (an antiquated medicine) in five years? It is of course possible that this physician's entire patient population has contained abnormally few hypertensives. It is also possible that this physician is not rendering "state to the art" patient service in this medical area.

The optimized and trained neural networks of the present invention are motivated by, and used for, improved patient care. However, improved patient care is not inconsistent with reduced costs, and cost control. In the first place, rendering any patient an optimally effective drug dosage for that patient may shorten the course of treatment, reduce patient non-compliance with prescribed drug therapies, reduce or eliminate undesirable side effects, and expedite cure. Consideration of the aggregate statistics of a great number of patients undergoing drug therapy at the level of, for example, a health maintenance organization or a governmental program such as Medicare, may permit the recognition of improved effective regimens of treatment, reducing cost attendant upon wastage. It is also at this high level where deviant drug prescription and/or consumption patterns and trends may be noticed, quantified and examined.

4. A Neural Network for Predicting an Optimal Dosage of a Particular Drug for a Particular Patient Therefore, in one of its aspects the present invention can be considered to be embodied in a computerized method of predicting an optimal dosage of a particular drug for a Particular Patient in consideration of previously determined optimal dosages of the drug for members of a patient population.

The computerized optimal drug dosage prediction method commences with the programming a neural network having an architecture of one or more slabs, the slabs collectively relating "input data" to "output data". The "input data" includes at least a selected three (3) of a person's traits drawn from at least two (2) of the three (3) groups consisting of Group 1 overt indications of (1a) age, (1b) gender, (1c) race, (1d) ethnicity, (1e) diet type, (1f) height, (1g) weight, and (1h) body surface area; Group 2 medical diagnostic indications of (2a) blood pressure, (2b) use of a drug other than the particular drug at the same time as use of the particular drug, (2c) fitness, (2d) peptide levels, and (2e) genetic predisposition to a particular disease; and Group 3 pharmacological indications of (3a) pharmacokinetic parameters, (3b) pharmacodynamic parameters. (It might be wondered just what is so important about "at least a selected three (3) of a person's traits drawn from at least two (2) of . . . [some] three (3) groups". The answer is: the number and diversity of traits are simply to help to quantitatively distinguish the present invention over previous dosage charts that may plot, by way of example, a family of curves relating recommended dosage by age, weight and sex (i.e., by three traits).)

The "output data" is the clinically-determined optimal drug dosage for the same person.

Each of the programmed neural networks is trained with a training data set drawn from a large number of historical medical records of a large number of persons historically administered the particular drug, the records relating the selected input data to the output data.

One of the neural networks that performs best on the training data set is selected, becoming a "selected trained neural network".

This selected trained neural network is thereafter used to predict an optimal dosage of the particular drug for the Particular Patient. This using transpires by inputting the selected input data—which input data is at least a selected three (3) of The Particular Patient's traits drawn from at least two (2) of the three (3) groups consisting of Group 1 overt indications and Group 2 medical diagnostic indications and Group 3 pharmacological indications—in order to ascertain as (2) output of the trained neural network the output data—which output data is the predicted optimal dosage for the Particular Patient.

The architectures of the plurality of neural networks are commonly, and preferably, established by a same human who does the programming of the neural network. One human thus acts as both neural network architect and neural network programmer.

The selecting step preferably consists of choosing one of the several neural networks by a genetic algorithm, the genetic algorithm acting to select that one of the plurality of neural networks that performs best on the training data set. The training of each of the plurality of neural architectures thus permits, along with the choosing, not only the selection of a single one of the plurality of neural networks that performs best on the training data set, but the training of this selected one of the plurality of neural networks to optimally relate the input data to the output data.

This computerized drug dosage prediction method of the present invention may be extended and expanded to account for interaction between at least two, a first and a second, drugs taken concurrently by the Particular Patient. In this case the extended method involves (i) performance of the programming, the training, the selecting and the using in respect of a first drug to predict in a first selected trained neural network an optimal dosage of the first drug for the Particular Patient, and (ii) performance of the programming, the training, the selecting and the using in respect of a second drug to predict in a second selected trained neural network an optimal dosage of the second drug for the Particular Patient.

Then a number of drug interaction neural networks—each having an architecture of one or more slabs collectively relating data inputs of the order of patient traits to data outputs in the form of clinically-determined optimal drug dosage for each drug—are trained. Each of the several drug interaction neural networks is so trained with a training data set drawn from a multiplicity of historical medical records of a multiplicity of persons historically administered the two particular drugs—these records relating the input data to the output data.

The training produces a number of trained drug interaction neural networks. That one of several trained drug interaction neural networks that performs best on the training data set is selected to become a "selected trained drug interaction neural network". This selected trained drug interaction neural network is then used to predict the optimal dosage of both the first and the second drug for the Particular Patient. By this expanded method each drug's optimal dosage may be predicted in respect of the other drug's optimal dosage.

5. A Neural Network for Predicting an Optimal Dosage of a Particular Drug for a Particular Patient in Terms of (i) Drug Efficacy and (ii) Drug Side Effects Therefore, in another of its aspects the present invention can still be considered to be embodied in a computerized method of predicting an optimal dosage of a particular drug for a Particular Patient, only in this case drug side effects, as well as drug dosage efficacy, are considered.

In this variant method of the present invention a neural net that relates drug dosage to both drug efficacy and to drug side effects is programmed. This neural network is trained in consideration of both (i) efficacy and (ii) side effect measures from usages of the drug at determined dosages on members of a population, producing by the training a trained neural network.

The trained neural network is subsequently usable to predict a drug dosage for an individual patient that (i) delivers adequate measures of efficacy while (ii) minimizing adverse side effects.

In fact, this using preferably involves exercising the trained neural network in respect of various drug dosages to assess the (i) measures of efficacy and (ii) adverse side effects in respect of each of a number of drug dosages, ultimately selecting the drug dosage for the Particular Patient that (i) delivers the adequate measures of efficacy while (ii) minimizing the adverse side effects.

6. Extension of Drug Dosage Methods of the Present Invention to Diet Management In still yet another of its aspects the present invention can still be considered to be embodied in a computerized method of diet and/or exercise management.

In the computerized method the effect(s) of one or both of dietary items consumed or exercises performed on the measured physiological characteristics of a Particular Patient is predicted. The method consists of first programming a neural net that relates any of selected dietary items consumed and exercises performed on measured physiological characteristics of patients as might be expected to be affected by the selected dietary items and exercises. The neural network is then trained in consideration of historical data on the impact of the dietary items consumed and exercises performed on the physiological characteristics evidenced by members of a population, therein to produce a trained neural network. Finally, the trained neural network is used to predict the change in physiological characteristics to be anticipated for an individual Particular Patient who consumes any of the selected dietary items and/or performs any of the selected exercises.

The neural network may optionally be repeatedly exercised in respect of various selected dietary items consumed and/or selected exercises performed to assess the (i) measures of efficacy and (ii) adverse side effects in respect of each selected dietary item consumed and/or selected exercise performed. These exercises ultimately permit selecting dietary items and/or exercises that will (i) deliver adequate measures of efficacy to the Particular Patient while (ii)

maximizing acceptability and suitability to the Particular Patient's preferences and demonstrated conduct.

These and other aspects and attributes of the present invention will become increasingly clear upon reference to the following drawings and accompanying specification.

BRIEF DESCRIPTION OF THE DRAWINGS

FIG. 6 shows a Table 1 giving a brief overview of the main differences between Darwinian evolutionary theory and most present day Genetic Algorithms (GAs).

DESCRIPTION OF THE PREFERRED EMBODIMENT

The present invention includes a trained neural network as part of its method and system. The neural network used is a mapping net: a supervised, feed forward neural network. The net models an example data group which consists of a series of correct example patient data sets. Each example patient data set includes (i) example patient information input data and (ii) corresponding example patient information output data. The example patient information input data and corresponding output data are organized in categories. The categories classified as "input data" may include patient (i) age, (ii) sex, (iii) ethnicity, and (iv) the prescribed amount of the drug(s) of interest. The categories classified as "output data" may include drug side effects and drug effectiveness.

The process of modeling the example data sets (the example data group) is referred to as "training the neural net". The process of training the neural net can be described as fitting each individual example data set which makes up the example data group. To fit the data, the neural net uses a fitting function to perform a nonlinear least squares regression on the given data set. During each run, the net's free parameters (weights) are varied to minimize its chi squared error in modeling the example data group. The exact fitting function is complicated by the fact that it incorporates (i) many free parameters, (ii) multiple applications of a simple nonlinear function, and (iii) multiple linear combinations of intermediate quantities. The nonlinear function repeatedly used (the "transfer function") is a sigmoid function, which varies monotonically between 0 and 1. The multiple linear combinations combine the free parameters with the transfer function values.

1. Theory and Practice of the Present Invention

Figure 1:
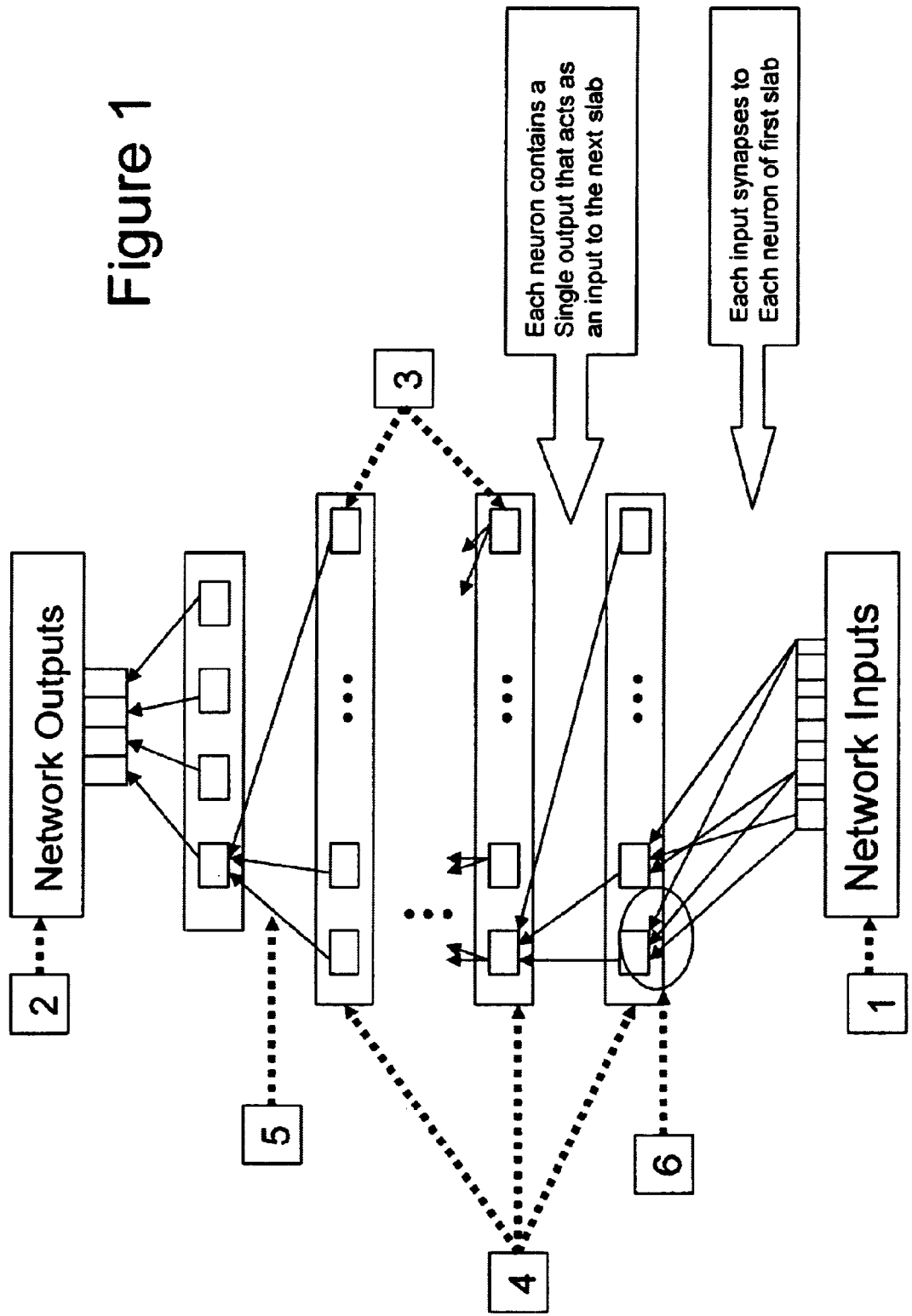
FIG. 1 is a diagrammatical depiction of the modeling of the patient information used in the present invention.

Because the preferred process of the present invention used to model the example data sets is complicated, some of its features are diagrammatically illustrated. Referring to FIG. 1, a few key features in the diagram are the network inputs 1, outputs 2, nodes 3, and slabs 4. The network inputs 1 are indicated by the line segments and the box at the bottom of the FIG. 1, and the network outputs 2, by the lines and box at the top. Individual rectangles, called nodes 3 or neurons 3, represent application of the transfer function (such as a sigmoid function), with the result 5 denoted by a line segment above the neuron. The convergence of multiple line segments 6 at the bottom of a given neuron indicates that a linear combination, with weights stored locally in the neurons, is to be applied before applying the neuron's transfer function.

Various algorithms can be used to optimize the fitting function implemented by the entire network. A standard technique is to use backpropagation. It is preferred, however, to use global optimization, preferably with a Levenberg-Marquardt algorithm, and still more preferably a Levenberg-Marquardt algorithm in combination with a family of simulated annealing algorithms. The Levenberg-Marquardt (LM) algorithm increases net training speed by using an analytic approximation. See Ojala, P., Saarinen, J., & Elo, P. (1995); Novel technology independent neural network approach on device modeling interface; *Circuits, Devices and Systems*, 142, 74–82. As one takes small steps downhill in error surface, this algorithm approximates the form of the error surface near local minima as a "bowl" (a quadratic form). It then analytically determines the location of the bottom of this bowl, and uses this location to avoid laboriously single-stepping to this (most likely spurious) minimum. It also provides an accounting mechanism for determining how large a step one should take in the direction of this minimum.

The simulated annealing algorithms use a different approach. They add a small amount of thermal (random) noise to the net's weights, and keep the changes if neural net performance improves. See Treadgold, N. K., & Gedeon, T. D. (1998); Simulated annealing and weight decay in adaptive learning: the SARPROP algorithm. *IEEE Transactions on Neural Networks*, 9, 662–668.

The temperature of the perturbations (i.e. the magnitude of random noise) to the weights is gradually decreased to allow the net to settle into a nearly global minimum of error surface rather than getting stuck in local minima. One problem with this algorithm, however, is that it does not calculate gradients of the error surface. The algorithm thus lacks efficiency at settling to individual local minima.

The advantage, however, is that many such minima are explored simultaneously. Accordingly, even though individual minima are not well optimized, the net will migrate to better local minima. The preferred combination of the annealing and Levenberg-Marquardt algorithms (1) achieves the speed of the directed error minimization associated with the Levenberg-Marquardt algorithm, while (2) retaining the ability to "jiggle" fitting parameters out of local minima associated with simulated annealing. The result is a fast least squares fitting routine that avoids local minima as false solutions.

Although the LM algorithm was designed to be used for functions with many free parameters, it is not a practical method for optimizing functions with as many free parameters as a moderately sized mapping neural net. The reason is that it requires that a linear matrix equation be solved in determining the direction in which to vary the weights. The dimension of the matrix in the equation is the number of free parameters N in the neural net. For a net with 10 inputs, a pair of hidden slabs each with 100 neurons, and 5 outputs, the number of free parameters is roughly $10*100+100*100+100*5$, or about $10^4$. (There is actually an additional free parameter, a bias term, in each neuron.) This means that N is roughly $10^4$. Solving a general matrix equation (with no special symmetries) costs of order $N^3$ operations, and requires storage of $N_2$ double precision floating point numbers. The memory required can be estimated as (8 bytes/double)*$((10^4)^2$ doubles)/$(10^6$ bytes/Megabyte)=800 Megs RAM. Implementations of the LM algorithm typically require storage for two matrices, doubling the memory requirements. This already far exceeds any PC's RAM capacity. We believe required processing time and memory render the LM algorithm incapable of practical use in training large nets.

To overcome the limitations of the standard LM algorithm, the inventors developed a method to reduce the required memory and time associated with the standard LM algorithm. In the method developed, instead of varying all of a function's free parameters at once during a run one varies only a fraction of them at a time. During each run, the remaining non-varied free parameters are treated as fixed parameters of the fitting function. Thus, during each run, a standard LM algorithm is applied to a fitting function with many fewer free parameters. The run is repeated a sufficient amount of times to vary each parameter many times. The inventors believe that a sufficient amount of times to vary a parameter is of the order of 1: that is, between 1 and 10. By varying parameters in a step wise or partitioned fashion (only a fraction f of the parameters at a time), the memory required to perform the fitting drops by a factor of $f_2$, from of order $N_2$ to $(fN)_2$ Processing time drops from of order $N_3$ to of order $(fN)_3/f=f_2N_3$, a savings of $f_2$. Accordingly, both memory and processing time are reduced.

The process developed to reduce required time and memory uses an algorithm that is called "a partitioned Levenberg-Marquardt Algorithm (pLM)". The improvement associated with pLM comes with a cost. Since some arbitrary pairs of weights never get varied together, the pLM can never achieve the level of optimization attained by use of the full LM. However, the inventors believe that pLM performance approaches that of full LM in the limit that all weights are varied simultaneously. They believe that pLM provides a method of making Levenberg-Marquardt-type global optimization feasible for moderate to large sized neural nets.

Figure 2:
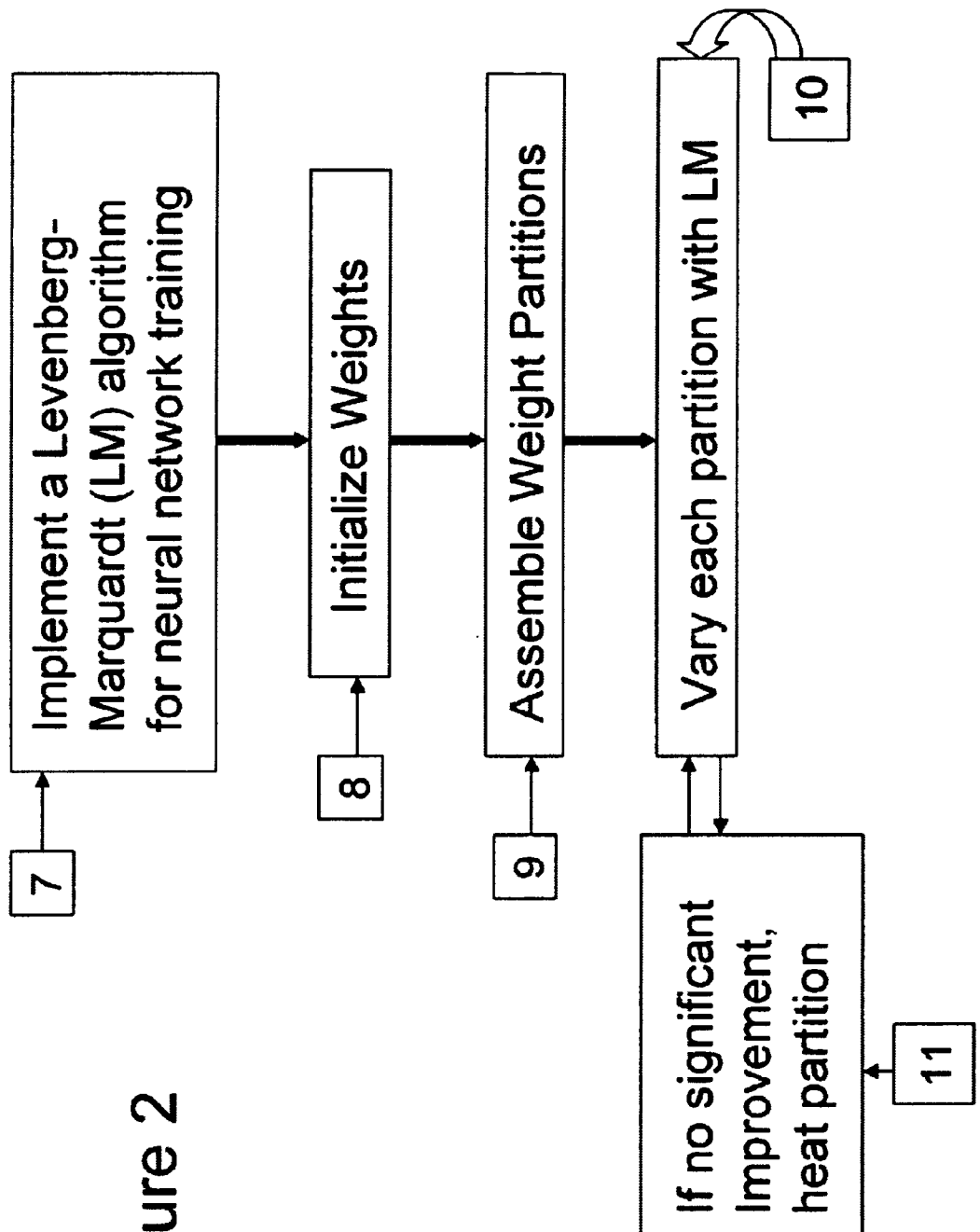
FIG. 2 is a diagrammatical depiction of the method of reducing computer time and memory required to model patient information used in the present invention.

FIG. 2 discloses, in flow chart fashion, the preferred method used to reduce the required memory and time needed to optimize the fitting function. Referring to FIG. 2, the Levenberg-Marquardt (LM) algorithm for use with training neural nets is implemented at 7. The LM global optimization algorithm minimizes a given function with one or more unspecified parameters. In the context of training neural nets, the given function is the "fitting function" of the mapping neural net.

The weights of the network are initialized at 8. One way of doing this is to choose the net weights at random. Alternatively, one can randomly initialize a predetermined number of times, keeping the best performing random weights for use in the pLM optimization. An entire simulated annealing algorithm may also be run to obtain a decent starting point.

Partitions of weights, which will be varied, are assembled at 9. In choosing the partitions of weights to vary, one must in principle ensure that every weight be varied multiple times. These partitions of weights may be chosen in a variety of ways. The combination of weights that the inventors believe should be varied is as follows:

First, the most significant fraction of weights in each slab should be varied; that is, those weights from each slab in whose direction the magnitude of the gradient of net error is larger than the corresponding values for other weights in the same slab. In other words, for each slab, for each weight, the derivative of net error with respect to the given weight is calculated. Then the magnitudes of these derivatives ares sorted. Choose, as weights to vary, those corresponding to the largest derivative magnitudes.

Next to be varied are a fraction of weights chosen at random from each slab.

Finally to be varied are the entire set of weights belonging to any sufficiently small slab. To see why this could be important, consider a slab in a large network that contains only a small number of neurons. For example, in data compression, a net mapping the identity function is forced to contain such a small slab. The weights in that small slab will strongly affect the net output. The inventors believe it is desirable to include those weights when setting any other weights in the net.

Each partition in turn is varied at 10. For each partition obtained in the varying step above all the weights—except for those in the given partition—are left fixed. The resulting fitting function (containing only as many free parameters as there are weights in the current partition) are fed to a standard LM algorithm. When the LM run is complete, again, all the weights of the network are fixed except those in the next partition. The process is repeated for each run until each weight has, on average, been varied a predetermined number of times. The number of times should be of order 1.

5) A partition, if its minimization fails, is shown to be "heated" at 11. If varying the weights in a given partition fails to improve the net error significantly, a small Gaussian random deviate is added to those weights, the net error is remeasured. This is done a predetermined (but small) number of times; times of order 1. The perturbed weights of the best performing resulting nets are kept.

After the neural net is trained, it is tested. To test, patient data sets which the inventors call "test data sets" are used. Each test data set, like each example patient data set, has patient information input data and corresponding patient information output data. The input data and corresponding output data for the test data sets are organized into the same categories of information as the example data sets. The test data sets should have example patient input data to which the net has not yet been exposed. As a first test step, input data from a test data set or sets is input into the trained net. The output of the network is an extrapolation by the network of patient information output data. The extrapolated patient information output data should correspond closely with the existing example output data from the test data set or sets. If it does not, either more training data, a different network size, or both may be needed to obtain better performance.

Testing the network yields a chi squared measure of error; better performing networks have a lower such error estimate. In principle, a perfect model, trained on a sufficiently great amount of training data and tested with a sufficiently large amount of testing data, would achieve a chi squared value of about 1. Practical models will perform worse than this, with larger chi squared values. Although the actual chi squared value achieved depends on the uncertainty estimates of the outputs for each patient data set, the inventors believe that a mapping net with a testing chi squared error of between 1 and 10 is acceptable. The training and testing should be performed by a neural net field expert, although rudimentary results may be obtained by someone merely capable of using neural net training software.

It is contemplated that a population of nets will be trained for a drug or set of drugs of interest. The population of nets will be tested and the neural net with the smallest error estimate will be used for the given drug or drugs of interest. The result is a different trained neural net for each drug or set of drugs of interest.

The following describes in more detail how to prepare the example data sets used to train the neural net and the test data sets used to test the neural net. As a first step, a clinician with experience in the drug or drugs of interest first determines relevant categories of information which seemingly have a bearing on determining acceptable drug dosage. The categories developed could fall into two groups: 1) categories of information which relate to factors which impact how well a drug works, and 2) categories of information which relate to factors which help assess how well a drug is working. The first group could include categories such as age, gender, height, ethnicity, dosage of drug of interest, dosages of drugs taken in conjunction with drug of interest, and various pre-treatment health characteristics such as blood pressure, weight, and glucose level. From preliminary results, the inventors believe that important characteristics often overlooked are (i) race and (ii) ethnicity. The categories in group 2 can include side effects (health characteristics during treatment such as nausea, headaches, vomiting, diarrhea etc.) and drug efficacy measures (such as symptom levels and pharmacokinetic peptide levels).

Each category should have associated with it a value scale to quantify the information. The value scale in many instances will be determined by the category of information. For instance, one category of information, blood pressure, could use as its value scale the numerical values used by physicians. Some categories of information, however, may not have a scale associated with the category. For instance, the category "ethnicity" does not have a ready scale. In this instance, a sliding numerical scale could be used to quantify ethnicity. For example the degree of a person's Japanese ethnicity could be quantified by determining, on a scale of 1 to 5 the person's degree of mixed ancestry. Alternatively, a simple yes (1) or no (0) numbering system could be used to account for ethnicity.

Once the categories have been determined, individual example data sets are made. Each example data set relates to a single example patient and includes individual fields to store information. Each field corresponds to a single category of information. The information is recorded in each field in a quantified manner in accordance with the particular value scale. As stated previously, for each data set, each category of information is classified as either example patient information input data or patient information output data. The example patient information input data, associated with each data set, includes information falling within the group 1 categories—information which impacts the effectiveness of the drug of interest. The example patient information output data, associated with each data set, includes information falling within the group 2 categories—information which helps assess how well a drug is working.

Once the individual data sets are prepared, they are categorized into (1) example data sets for training and (ii) test data sets for testing.

Figure 3:
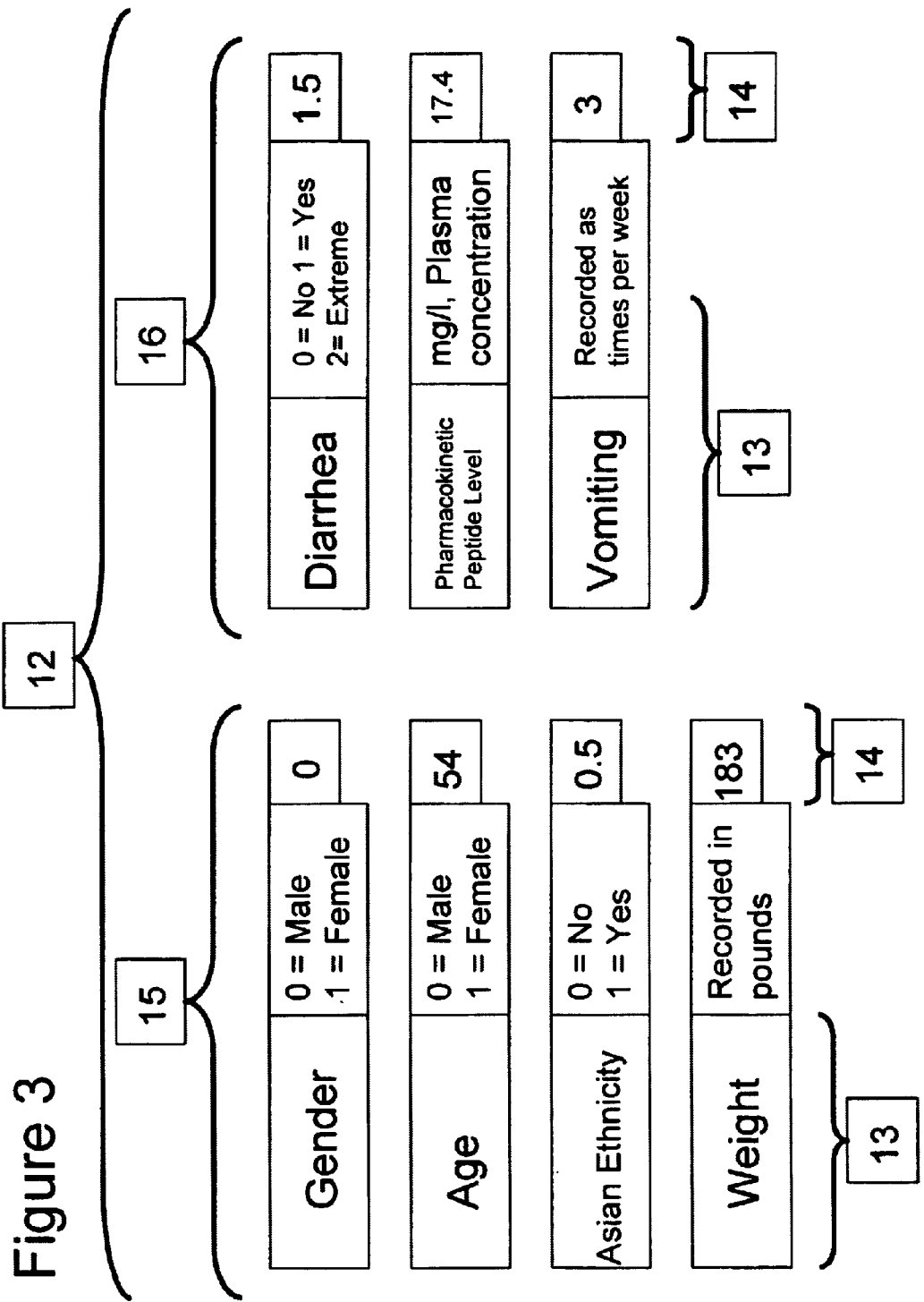
FIG. 3 is a depiction of a record which embodies an example data set.

FIG. 3 discloses a record 12 which embodies either an example or test data set. The categories of information 13 are shown beneath each categories corresponding field 14. The categories on the left side of the record are classified as the example patient information input data 15. The categories 13 on the right side of the record are classified as the example patient information output data 16. As stated each record corresponds to a single example patient. The shown record, shown for clarification, only includes some of the categories of information which could be recorded as example data input and example data output.

After the data sets are prepared and categorized, a computer programmer processes the data sets to a software construct appropriate for modeling and testing. It is contemplated that a determination of relevant categories for each drug of interest would be made by examining records of example patients. Additionally, the types of information stored in the various input fields would likely come from examining example patient histories.

Figure 4:
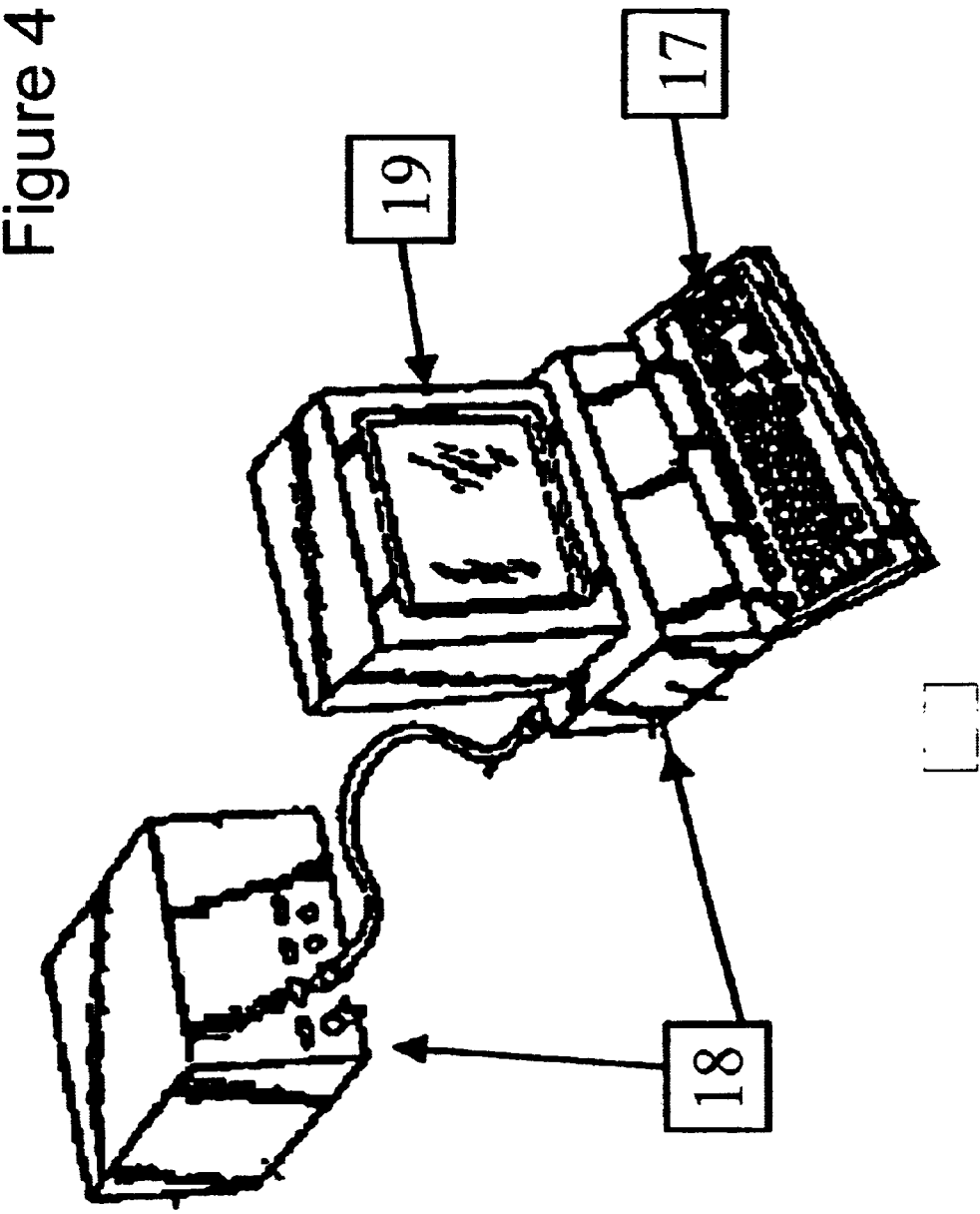
FIG. 4 is a schematic depiction of a display screen having post-training input data entered thereon.

FIG. 4 discloses the computerized system which models the input example data sets. The example data sets are input by an input device 17 into computer processing unit or units 18. These input example data sets are shown in FIG. 1 as network inputs. The CPU includes the software construct which models the input example data sets. The display 19 displays the modeled outputs, shown in FIG. 1 as network outputs. Once the neural net has been trained and tested it is ready for use as part of the drug dosage estimator system.

Figure 5:
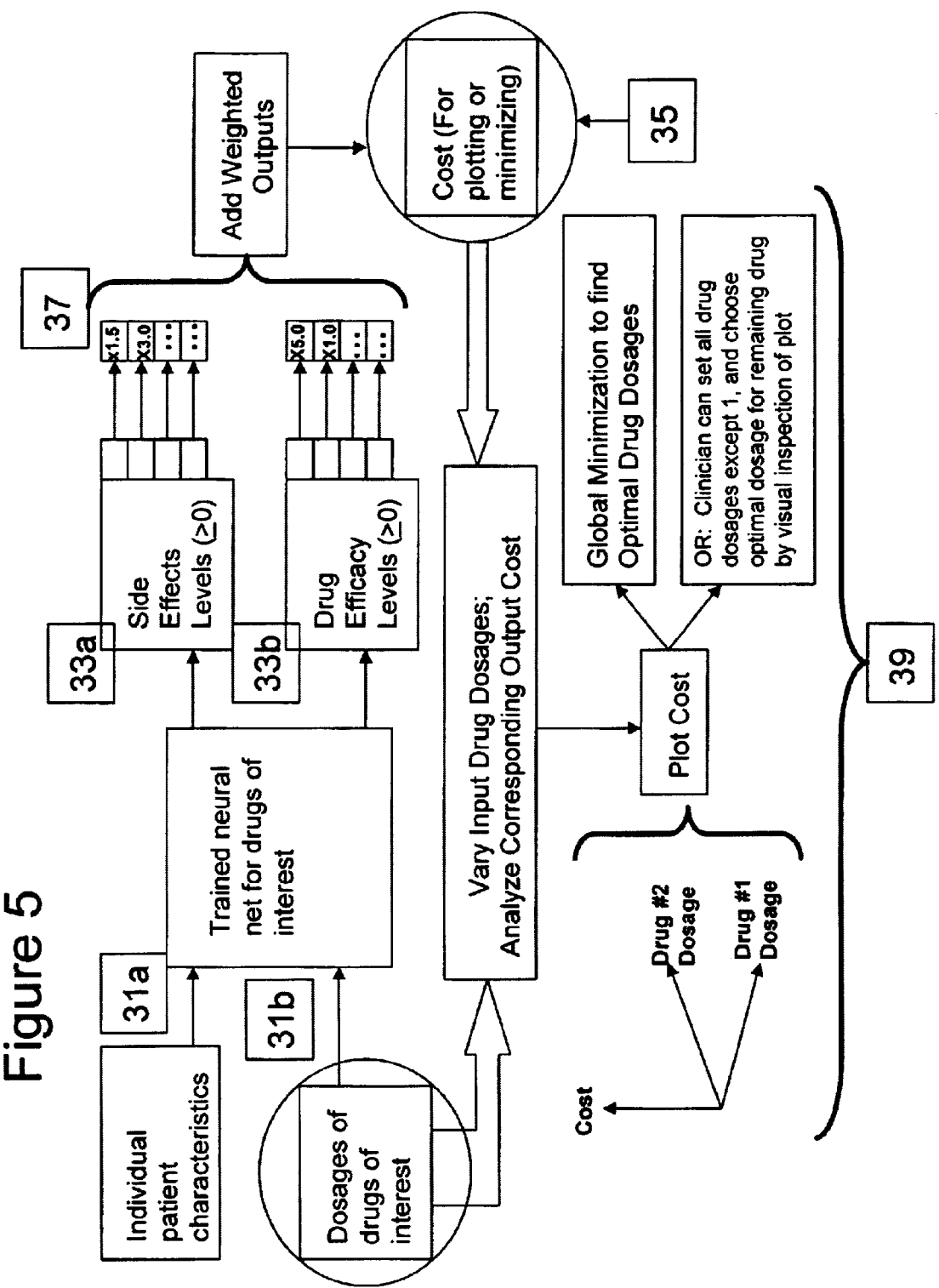
FIG. 5 is a diagrammatical depiction of the method of extrapolating patient information data output and converting the extrapolated information to a recommended drug dosage.

FIG. 5 discloses the computerized drug dosage estimator system. The system includes an input device 20, a computer processing unit or units 21, and an electronic display 22. The input device 20 allows for the input of the post-training input data about the patient. The categories used to organize the post-training input data include most of the categories used to organize the example patient information input data, excepting the category: dosage of drugs of interest. This category may be replaced by the category, drug dosage of interest start value. The same value scales used to quantify the example input data are the also used to quantify the post-training input data. The post-training input data is entered in the system through fields. Each category of information has a corresponding field. Each category of information is entered into its corresponding field through the input device. A clinician or physician would obtain, quantify, and enter the patients information in the appropriate fields.

FIG. 6 discloses the screen 25 of display 22. The screen displays the fields 27, 27a which correspond to categories 29 of the post-training patient input data 31a, 31c. The screen 25 shows the post-training patient information input data as a value scale.

Figure 7:
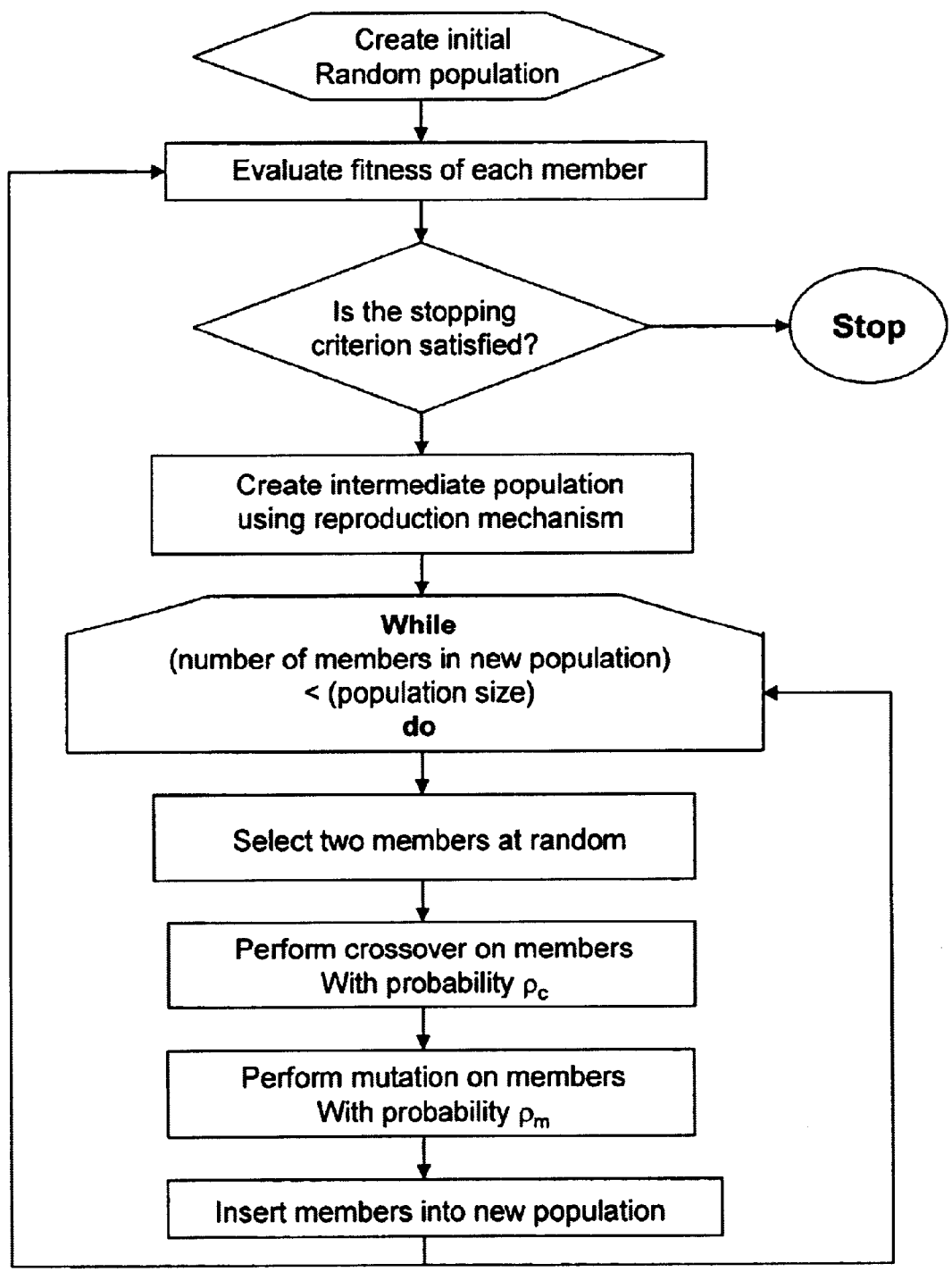
FIG. 7 shows the flowchart of the standard genetic algorithm.

Referring to FIG. 7, exactly how the computerized method and system extrapolates outputs and converts the extrapolated outputs into a recommended drug dosage can be seen in greater detail. As described above, the post training data inputs 31a are obtained from the specific patient and input into fields 27 by the treating physician. Additionally, the physician may input in field 27a drug of interest dosage start value 31c. The system uses the drug of interest dosage value 31c for generating dosage values 31b. After input of the data, the system extrapolates, nonlinearly, from the example data group, a plurality of groupings of extrapolated output data. Each grouping of extrapolated output data 33a, 33b is extrapolated to fit both the post-training input data 31a and one of said plurality of generated drug of interest dosage values 31b. Each grouping of extrapolated output data 33a, 33b includes an extrapolated side effect value 33a and extrapolated drug efficacy value 33b.

Each grouping of extrapolated output data is converted to a cost 35 with the aid of a cost function. The cost 35 is an increasing function of side effect values 33a and a decreasing function of drug efficacy values 33b. The relative weights 37 which correspond to the extrapolated outputs 33a, 33b should be incorporated in the cost function in the following form:

$$\text{cost} = \text{relative\_weights} \cdot \text{normalized\_outputs}$$

where:

Relative_weights [i] $\leq 0$ for efficacy outputs and $\geq 0$ for side effects outputs, with the (default) magnitudes of relative_weights [i] set by the clinical field expert to be larger for more important measures of efficacy. Note that these relative weights may also be set by the user of the dosage estimator after product delivery. In this way, predictions may be customized to the patient's or the clinician's personal priorities. "Normalized_outputs" are the neural net outputs scaled to [0,1] (the scaling being based on the training data set ranges if necessary). The "•" [a center dot] refers to the scalar dot product of vectors. This means each output is weighted separately.

The System as part of routine 39 (shown in FIG. 5) sequentially generates (i) dosage values for a number of drugs of interest, and (ii) the corresponding extrapolated groupings, and also obtains (iii) an extrapolated grouping having a minimum cost. The extrapolated grouping having the minimum cost has associated with it at least one of said plurality of drug of interest dosage values 31b. A standard global minimization algorithm is used to find the drug dosage yielding the global minimum in cost. The display 19 (shown in FIG. 14) shows the drug dosage, associated with the optimal extrapolated output, as a recommended dosage to the proscribing physician to guide the physician in writing the prescription for the patient.

Alternatively, for a given patient, the cost may be plotted against a range of said plurality of dosages, and the clinician can choose a global minimum and corresponding range by eye.

It is preferred that recommended drug dosage be in the form of a range. To attain ranges for each drug of interest, the other drug dosages used with the drug of interest are fixed to their global minimum values. The dosage of the drug of interest is then varied and the cost is monitored as the drug dosage is varied. The dosage is varied over its maximal range. An arbitrary threshold in the relative cost increase (such as 10% of the maximal range above the optimal cost of the global minimum) yields a criterion for reporting an optimal range of drug dosages for the given drug. The threshold can also be varied by the field clinician.

The preferred computerized drug dosage estimator—a computer program—uses a variety of computer languages. The graphical interface, front-end, of the computerized system can use a variety of windowing languages. It is preferred to use the g programming language associated with the LabView development environment. This has the advantage that it is a platform-independent windowing language: its use is not confined to the use of a particular operating system. Another advantage is that it is amenable to use over the Internet: the preferred software can be accessed through its graphical user interface from any machine equipped with a browser.

The neural net training software is preferably programmed in the C++ programming language. This is an industry-standard object-oriented language with limited text processing tools and no portable windowing capabilities. Its advantage is that it allows the programmer to take full advantage of the machine for performing mathematical calculations: the same algorithms implemented in g, for example, could take 10 to 100 times longer.

The preprocessing of the data sets is preferably performed with the Perl scripting language. This is a free language optimized for text processing: most automatically generated web pages are constructed with Perl scripts. The advantage for usage in the present invention is Perl's great functionality.

Standard neural nets yield no estimates of uncertainties. The inventors have, however, developed a simple method of estimating the variance in our neural net predictions. During network training, the training data set is used to set the weights, and chi squared values are calculated based on the performance of an intermediately trained net on the training data set. These chi squared values (or rather, the square root of chi squared per external degree of freedom) yield an estimate of the uncertainty of the outputs.

As the network settles down to an error minimum, these values can be interpreted to be variance measures of the network outputs when applied to a new, testing data set, assuming the training population and the testing population are drawn from a common parent population. Uncertainty estimates are thus obtained for the drug dosage predicted by the system. (A physician will recognize that this is of no small importance; both physician and patient alike are more comfortable with a drug the recommended dosage level of which is (i) of low uncertainty but (ii) high tolerance to non-optimal under-, and over-dosage. When this situation is not obtainable—as it often is not—then it is at least better to know what are the probabilities, and risks, associated with the recommended optimal drug dosage, or dosage range.)

The above methods and systems assume that a large amount of individual data sets will be used to form the example data group used for training. For instance, an acceptable level is normally a minimum of from 500 to 2,000 patient data sets depending on the drug and the complexity of its interaction(s), and is more commonly about 10,000 patient data sets. The method and system, however, can be modified to account for situations where only a small number of patient data sets compose the available example data group. In the modified system, all individual example data sets used for training have, as their example patient information output data, clinically determined optimal drug dosages. The output data does not include side effect values and drug efficacy values. The corresponding example data inputs for each individual data set still include patient characteristics. The example input, however, does not include a value for dosage of the drug of interest.

The extrapolation of the method of the present invention that is shown in FIG. 7 does not require a generated drug of interest dosage value 31b. In this modified scheme, the example data group may be smaller than the full method, because the net is being asked to model less information: the effects of non-optimal dosages do not need to be learned. The problem with this alternate technique is that it assumed clinicians have already experimentally determined optimal drug dosages for a series of individual patients.

2. Background to Neural Network Terminology as Used in the Present Specification It should be noted that the numerical analytical techniques which are used in the present invention cover a family of techniques broadly referred to as neural networks. All of these techniques have a plurality of inputs and a plurality of outputs, and all involve the application of a number of subsidiary functions. These subsidiary functions are implemented with neurons and include multiple "transfer functions". These transfer functions in turn include linear combinations of other subsidiary quantities. Both the transfer functions and their linear combinations have initially unspecified parameters.

An ambiguity in terminology arises in the method in which these parameters are set, a process called "training". Some authors, such as Hecht-Nielsen, have limited the technical definition of a neural net to one whose training is defined entirely in terms of local operations, implemented with a "learning rule". These local operations are in turn defined in terms of only a subset of all the intermediate quantities of the net: the rule for modifying one parameter is based on the values of a few other parameters, rather than directly on the values of the network outputs. Examples of this local training principle are all traditional mapping neural nets, such as the backpropagation network and the perceptron.

Other training techniques are said to be "global": they specify methods of setting all of the net parameters at once by direct reference to the network outputs. Examples of these training techniques are global optimization algorithms such as Levenberg-Marquardt, simplex minimization, and simulated annealing. As a general rule, global techniques are less well studied than local techniques.

Although there are academic differences between these analytical techniques, the relevant features for purposes of the invention are as described above: they are all methods of mapping a plurality of inputs to a plurality of outputs based on examples in the form of training data.

3. The Theoretical and Practical Basis of the Present Invention

The objective of the present invention is to deliver into the service of medicine new computational tools useful to view and to evaluate historical medical data in different ways, and to query the data to learn of new relationships. The medical data includes, but is not limited to, voluminous historical data on the effects of drugs. A computational tool dealing with such data would desirably be able to do any of recognize, quantify and illuminate (i) patient characteristics—drug dosage relationships, (ii) patient characteristics—adverse drug reaction(s) associations, (iii) the sensitivity of both effective response(s), and undesired side effects, to various drug dosage levels, and (iv) interaction(s) between multiple drugs taken at the same time.

The new computational tools of the present invention provide an essential link between the work of the medical research groups where pharmacological relationships may be hypothesized and projected (i.e., adult male should take 1 gram medicine A daily for 10 days) and historical medical databases (i.e., for 94% of 241 adult males taking medicine B, 1 gram daily for 10 days was an effective safe dosage).

The computational tools of the present invention are based on computerized neural network techniques. They will in particular rigorously correlate drug response phenotype with genotype as well as other mitigating factors (e.g., age, weight, and diagnosis). The non-linear model of the present invention is ideal for such complex situations that involve multiple predictors. The computational models of the present invention—trained selected neural networks (being software programs that run in computers)—permit greater accuracy in the prescription of medications in the clinical arena.

Historically, while numerous factors have been shown to influence clinical drug response, the present invention is the first systemic approach to rigorously investigating the simultaneous interaction of these variables. For example, body weight may be of greater importance than the form of isoenzyme for a Caucasian male, while the converse may be true for an African American female. By simultaneously processing independent variables in parallel, the neural networks of the present invention can assign different weights for each variable and can adjust these weights according to varying situations.

The recognition and selection of neural networks that work—"optimal" neural networks—is normally a straightforward task for a human. However, it is somewhat more difficult, and uncertain, to architect the neural network, or a number of competing neural networks, in the first place. To optimize the neural net architectures of the present invention, use of a genetic algorithm (GA) is taught. Such a genetic algorithm is a technique recently developed by the computer science community and is not a reference to biological genetics, as will be explained in greater detail below.

In addition to parallel processing, a main advantage of the neural networks of the present invention over such linear programs as have previously existed is that the neural networks can integrate the features of a non-comprehensive set of test cases and apply them to new but related cases. For example, it may be impossible to provide a training case of each permutation of variables, but a neural network can extrapolate this information from prior "learning." The disadvantage is that this observationally-based predictive power is accompanied by a disregard for the identification of mechanisms underlying the predictions. However, this problem can be overcome by creating a "dummy" population data set once the neural network has been trained in order to determine the variance accounted for by a specific variable.

In the present invention, optimal drug dosage ranges are based upon clinically determined optimal drug dosages observed for a training population consisting of representative patients with characteristics spanning a wide range of input variables specifically including sex, race and age. As a result, women, minorities, and the elderly, who often require lower doses of medications—especially psychotropic medications—than do their Caucasian male counterparts, benefit greatly from more precise clinical guidelines of the present invention than those guidelines that currently exist of this population.

4. Background to, and Significance of, the Present Invention

The present invention combines the relevant variables of prescribing drugs into a single empirical model linking drug response phenotype to genotype, refining clinical prescribing practices, and facilitating future hypothesis testing regarding the underlying mechanisms of each component. This empirical model is a (i) selected optimal, (ii) trained, neural network.

Neural networks, or "neural nets", have existed since the 1960's, but their usefulness in medical applications is only beginning (CIRCA 1999) to be explored. While the earliest studies of the past decade have been related to the formulation of accurate diagnoses, the past two to three years have produced a proliferation of studies in the application of neural nets to clinical pharmacology. For example, neural networks are now being used to automate the regulation of anesthesia, to determine optimal insulin regimens, and to predict clinical response to other medications.

As an example of the latter, one study compared the use of a particular neural network (feedforward, back propagation) with a nonlinear mixed effect model (NONMEM) as a control. In prediction of gentamicin peak and trough levels, the neural network model was found to be substantially more accurate than the NONMEM.

In addition, recent research has featured the use of neural nets in the stabilization of insulin-dependent diabetes. As with may other medications, prescribing practices with insulin rely mostly upon the experience of the clinician as well as trial-and-error. In three independent studies, researchers were able to demonstrate the usefulness of a neural net model in predicting optimal insulin regimens for diabetics based upon demographic variables.

As research with neural nets begins to extend to various branches of medicine, the types of neural network models being used in medicine are slowly becoming more complex. For example, the addition of a genetic algorithm (GA) to a neural network has recently been shown to significantly reduce the error in prediction of clinical drug response. However, most current models used in research are dated and not as efficient or sophisticated as those yet to be publicized such as the Levenberg-Marquardt technique that is preferred for use in the present invention, and which is explained in detail below (see Background of Neural Networks, next).

5. Background to Neural Networks

A (mapping) neural net is a method of performing a nonlinear least squares fit to a given data set. The data set consists of examples of correct input/output pairs, whose features the neural net will "learn" during training. The inputs may consist of continuous quantities, such as age, weight, height, or quantities derived therefrom, or of fuzzy inputs. The latter may assume a continuous range of values, but only have well-defined meanings for a discrete set of values. For example, the property of being Hispanic could be modeled with a fuzzy input, with the discrete values 0 and 1 indicating the presence or absence of this property, but intermediate values could be used for a person with some Hispanic identity.

The form of the fitting function used for the least squares regression is generic, in the sense that a sufficiently large network can model a continuous function to any desired precision. The exact fitting function used is complicated by the fact that it incorporates many free parameters, multiple applications of a simple nonlinear function, and multiple linear combinations of intermediate quantities. The free parameters are set during training of the network; the nonlinear function repeatedly used (the transfer function) is typically a sigmoid function, which varies monotonically between 0 and 1; the multiple linear combinations combine the free parameters with the transfer function values.

Because the functional form of the fitting function is so complicated, it is typically denoted in a diagram as in FIG. 1. A few key features of this diagram are the network inputs, outputs, nodes, slabs, and evaluation of linear combinations. The network inputs are indicated by the line segments at the bottom of the FIG. 1, and the network outputs by those at the top. The individual rectangles, called nodes or neurons, represent application of the transfer function, with the result denoted by a line segment above the neuron. The convergence of multiple line segments at the bottom of a given neuron indicates that a linear combination (with weights stored locally in the neurons) is to be applied before applying the neuron's transfer function. Although these network architecture diagrams are a hallmark of mapping neural nets, they do not illuminate the utility of these computational structures.

The reason neural nets are useful is that they offer a generic method of modeling data and immediately yield a method of nonlinearly extrapolating that data. Given a list of examples of correct input/output pairs, a neural net is trained by systematically varying its free parameters (weights) to minimize its chi-squared error in modeling the training data set. Once these optimal weights have been determined, the trained net can be used as a model of the training data set. If inputs from the training data are fed to the neural net, the net output will be roughly the correct output contained in the training data. The nonlinear interpolating ability manifests itself when one feeds the net sets of inputs for which no examples appeared in the training data. The net still produces output drug dosages in this case; they are based on features extracted from related input/output pairs in the training data. A neural net "learns" enough features of the training data set to completely reproduce it (up to the variance contained within the data); the trained form of the net acts as a black box that produces outputs based on the training data.

There are a variety of methods to train these neural nets. The goal of each is the same: to vary the weights of the network to minimize the chi squared error of the network with respect to a given training data set. Traditional neural net training algorithms accomplish this in a slow, inefficient manner by taking single steps downhill in error surface. All the weights of the network are repeatedly varied slightly to reduce the overall error of the network slightly. Existing, publicly available neural net software is generally based on this single stepping downhill in error surface.

Global techniques have been found in recent years to achieve the error minimization much more efficiently than the old standard single-stepping downhill in error surface. These techniques have the disadvantage that the computations are no longer local and are therefore much more difficult to implement and academically less interesting. These methods have not yet been extensively developed and are not generally available outside of research contexts. If speed is required, these techniques must generally be custom developed. Furthermore, these newest methods are still (circa 1999) an active area of research and unstandardized: there is an art to choosing the specific form of the algorithms to use, and a neural net specialist is required.

Two of these global techniques are the Levenberg-Marquardt and (a family of) simulated annealing algorithms. The Levenberg-Marquardt algorithm increases net training speed by taking small steps downhill in error surface, approximating the form of the error surface near local minima as a "bowl" (a quadratic form), and analytically determining the location of the bottom of this bowl.

The simulated annealing algorithms use a different approach. They add a small amount of thermal (random) noise to the net's weights, and keep the changes if net performance improves. The temperature of the perturbations (i.e. the magnitude of random perturbations) to the weights is gradually decreased to allow the net to settle into a nearly global minimum of error surface rather than getting stuck in local minima.

The use of the more recent but non-standard global optimization techniques increases training speed dramatically (often more than two orders of magnitude) as illustrated in FIG. 2, making feasible the optimization of network architecture with a genetic algorithm. Needless to say, these optimization techniques are preferred in the present invention.

6. Genetic Algorithms

The optimized neural net architectures of the present invention are original—as are the (i) construction, (ii) training, and (iii) use of these architectures.

Genetic algorithms (GAs) were, however, developed by John Holland in the 1970's. GAs are based on a Darwinian-type survival-of-the-fittest strategy with sexual reproduction, whereby stronger individuals in the population have a higher chance of creating offspring. Each individual in the population represents a potential solution to the problem that is to be solved. The individuals are represented in the genetic algorithm by means of a linear string similar to the way genetic information is coded in organisms as chromosomes. In GA terminology, the members of a population are therefore referred to as chromosomes. Chromosomes are made up of a set of genes, and in the traditional case of binary strings these genes are just bits.

In biological systems from which the genetic algorithm terminology originates, a genotype, or the total genetic package, is a structure made up of several chromosomes. The phenotype is the actual organism formed by the interaction of the genotype with its environment. In genetic algorithms however, an individual is usually represented by a single chromosome, and therefore the chromosome and the genotype are one and the same.

A GA is sometimes compared to a Darwin model of evolution. The main overall difference between the two systems lies in their goals, (or rather the lack of one in Darwinian evolutionary theory). While in evolutionary computation the goal almost always is the optimization of some kind of fixed problem, this does not necessarily seem to be the case for biological evolutionary systems. Still, the success of evolutionary computation as a function optimizer, as reported on a wide variety of problems and in some parts supported by theoretical foundation, indicates that many features of Darwinism lend themselves very well for this purpose.

The aim of the genetic algorithm is to find an individual with a maximum fitness by means of a stochastic global search of the solution space.

The following steps describe the operation of the standard genetic algorithm.

1. Randomly generate an initial population of chromosomes.
2. Compute the fitness of every member of the current population.
3. Make an intermediate population by extracting members out of the current population by means of the reproduction operator.
4. Generate the new population by applying the genetic operators (crossover, mutation) to this intermediate population
5. If there is a member of the current population that satisfies the problem requirements then stop. Otherwise return to step 2

The reproduction (or selection) operator that is most commonly used is the roulette wheel method, where members of a population are extracted using a probabilistic Monte Carlo procedure based on their average fitness. For example, a chromosome with a fitness of 20% of the total fitness of a population will, on an average, make up 20% of the intermediate generation. Apart from the roulette wheel method many other selection schemes are possible.

The heuristics of GAs are mainly based on reproduction and on the crossover operator, and only on a very small scale on the mutation operator. The crossover operator exchanges parts of the chromosomes (strings) of two randomly chosen members in the intermediate population and the newly created chromosomes are placed into the new population. Sometimes instead of two, only one newly created chromosome is put into the new population; the other one is discarded. The mutation operator works only on a single chromosome and randomly alters some part of the representation string. Both operators (and sometimes more) are applied with a certain probability. FIG. 3 shows the flowchart of the standard genetic algorithm.

The stopping criterion is usually set to that point in time when an individual that gives an adequate solution to the problem has been found or simply when a set number of generations has been run. It can also be set equal to the point where the population has converged to a single solution. A gene is said to have converged when 95% of the population of chromosomes share the same value of that gene. Ideally, the GA will converge to the optimal solution; sometimes however a premature convergence to a sub-optimal solution is observed.

7. Uncertainty Estimates from Neural Nets Uniquely in Accordance with the Present Invention Standard neural nets yield no estimates of uncertainties, primarily because they are not a focus of concern in standard neural net applications. But clinicians will require such estimates. For example, if they try the optimal (mean) drug dosage predicted by a trained selected neural network of the present invention, and then decide that more or less is required, then they need to know how by much to change the prescribed dosage.

The present invention incorporates a simple, and arguably elegant, method of estimating the variance in the predictions of neural nets realized by the invention. During network training, chi squared values are calculated for the performance of the net on the entire training data set. As the network settles down to an error minimum, these values can be interpreted to be variance measures of the network outputs when applied to a new, testing population of patients, assuming the training population and the testing population are drawn from a common parent population. The present invention thus obtains uncertainty estimates on the drug dosage predictions output from the (trained selected) neural networks of the invention.

8.1 Use of the Neural Nets of the Present Invention in Hypothesis Testing

According to the literature, an intrinsic limitation of the use of neural nets is that they cannot be used to identify causal mechanisms underlying the predictions. This is a restatement of the generally accepted fact that the neurocomputing field cannot translate the mechanism a trained net uses to a list of causal statements about the system. Although the purpose of the proposed project is outcome-based in providing clinical guidelines for prescribing clinicians, it has occurred to the inventors that despite the fact that neither they nor anyone else can understand exactly how a neural net works, the neural network can be treated as a black box that models experimental data and used to probe that experimental data.

In this spirit, the inventors have conducted a numerical experiment using a trained neural net to approximate the real system. This experiment consists of the construction of a pair of artificial groups of patients with average characteristics chosen by the experimenter. For example, one group will consist entirely of males, and the other of females, although individuals within the artificial groups would differ in age and ethnicity. An average of the outputs of the trained neural net for these populations then permits comparison of the two artificial groups to determine whether they might originate from the same or different population domain. In the example, this process permits comparison, based on real experimental data, of optimal drug dosages for males and females. This demonstrates how one could test such a hypothesis a: "Do males need more of this drug than do females?"

8.2 Neural Network Based Optimal Drug Dosage Prediction of the Present Invention for Multiple Drugs Further diagrams of the steps involved in optimal drug dosage prediction using neural networks prepared (programmed), exercised and used in accordance with the present invention are shown in FIGS. 9–12. Diagrams 11 and 12 are particularly for the estimation of the dosage of multiple drugs.

Figure 8:
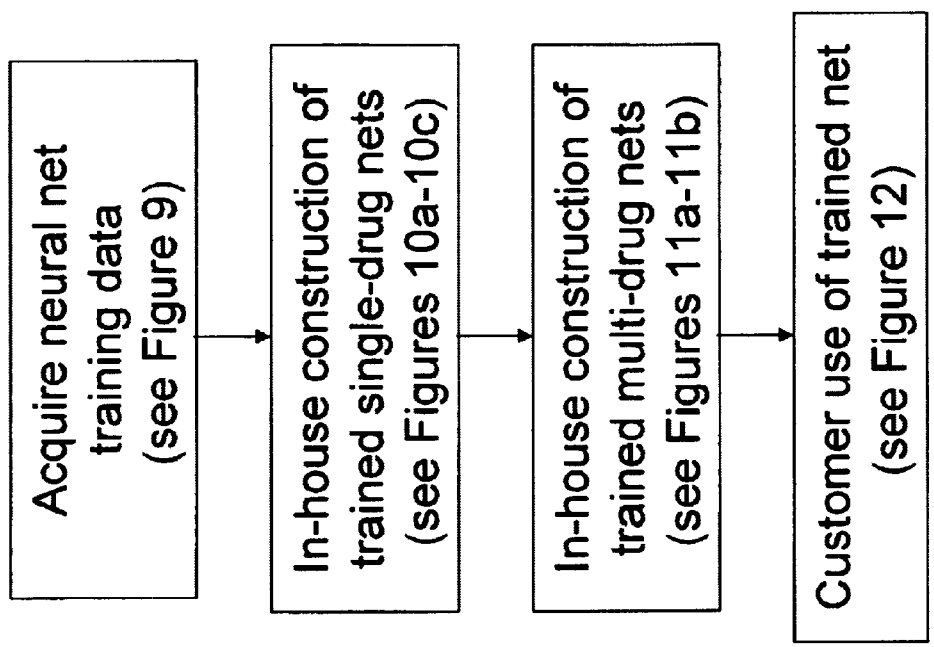
FIG. 8 is a top-level block diagram of the logical structure of a drug dosage estimator in accordance with the present invention, referencing the FIGS. 9, 10a–10c, 11a–11b, and 12 to follow.

A top-level block diagram of the logical structure of a multiple drug dosage estimator in accordance with the present invention is shown in FIG. 8. This FIG. 8 references FIGS. 9, 11a–10c, 11a–11b, and 12 to follow.

Figure 9:
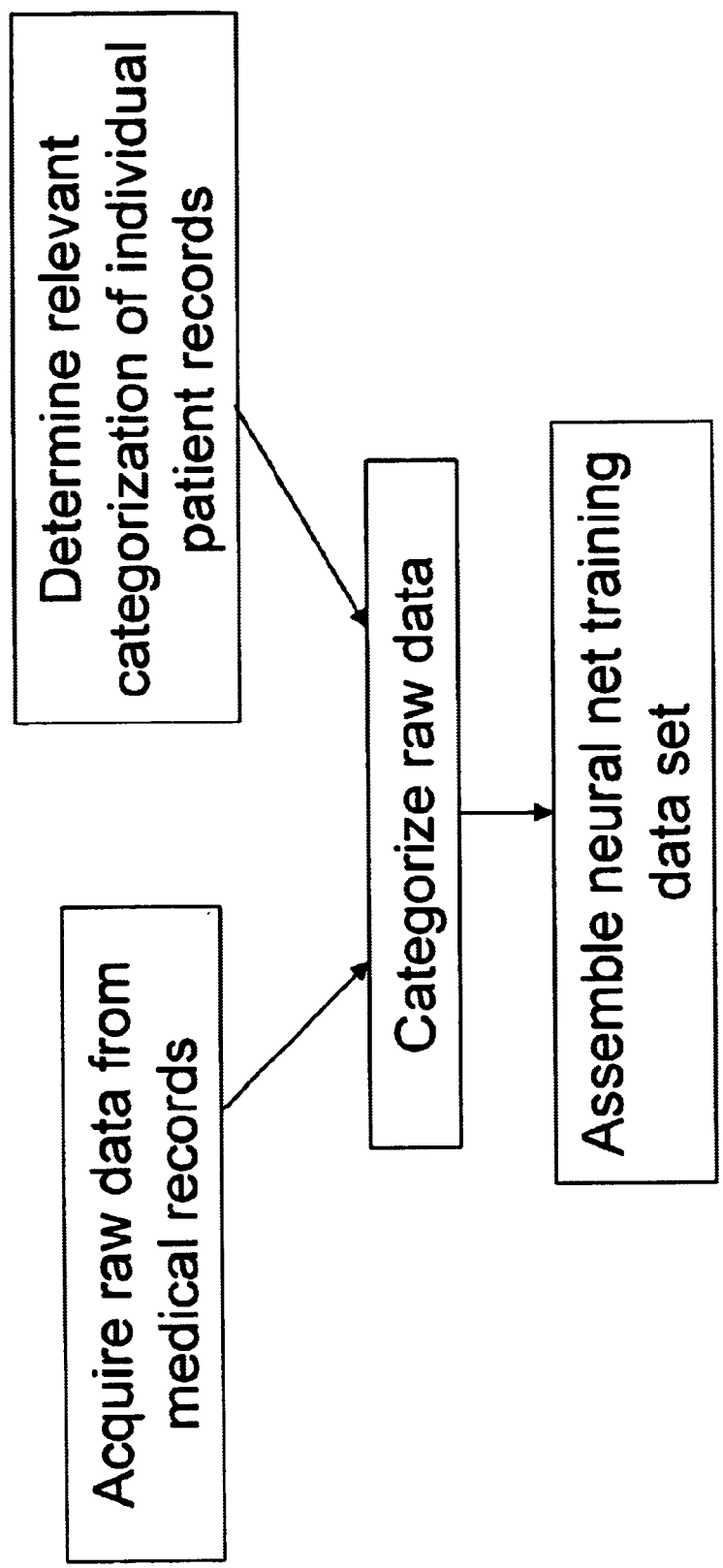
FIG. 9 is a block diagram of the acquisition of neural network training data in the drug dosage estimator in accordance with the present invention.

A block diagram of the acquisition of neural network training data in the drug dosage estimator in accordance with the present invention is shown in FIG. 9.

Figure 10A:
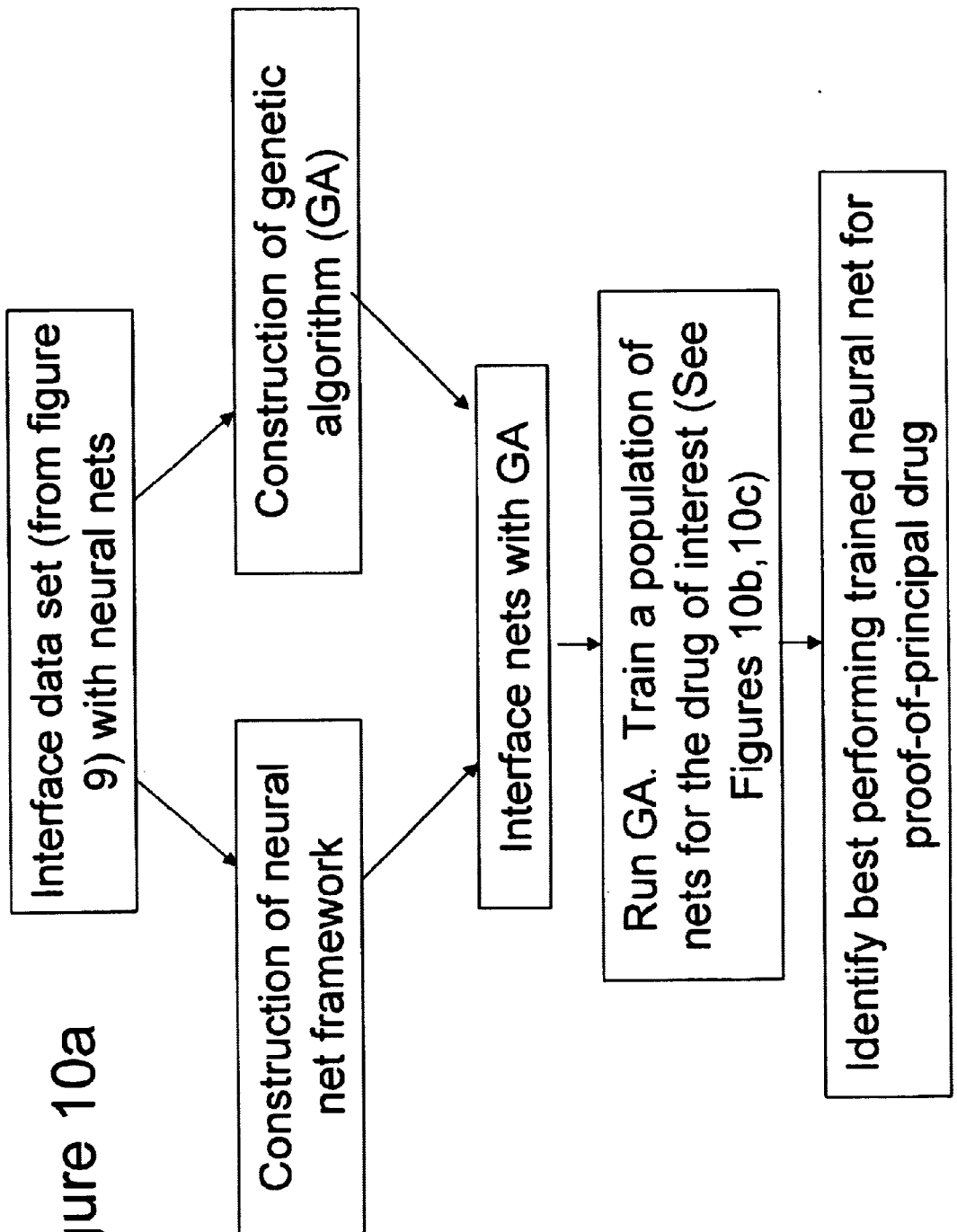
FIG. 10a is a block diagram of the construction of a trained single-drug neural network of the drug dosage estimator in accordance with the present invention.
Figure 10B:
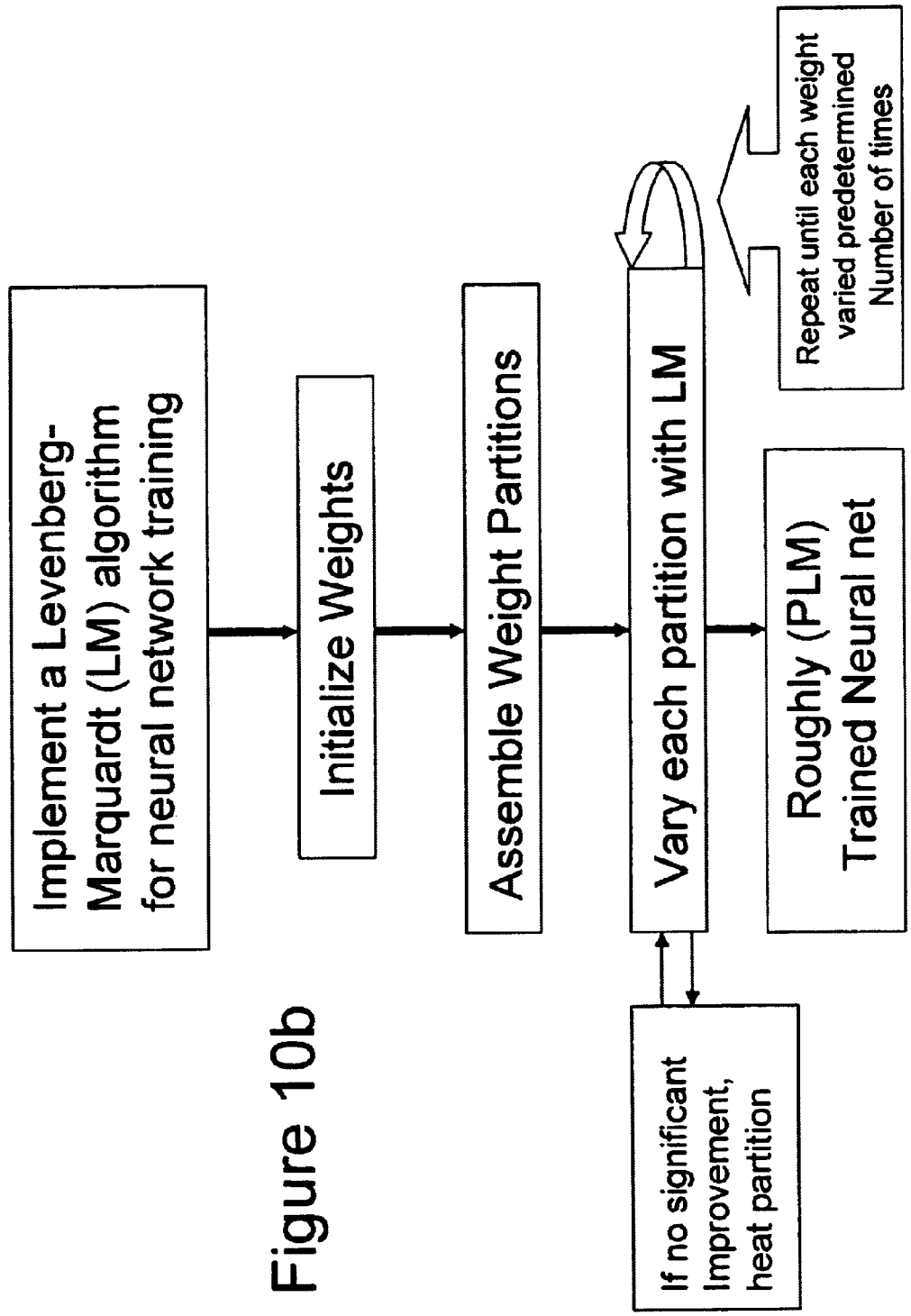
FIG. 10b is a block diagram of the construction of the Partitioned Levenberg-Marquardt (pLM) global optimization method of the neural network of the drug dosage estimator in accordance with the present invention.
Figure 10C:
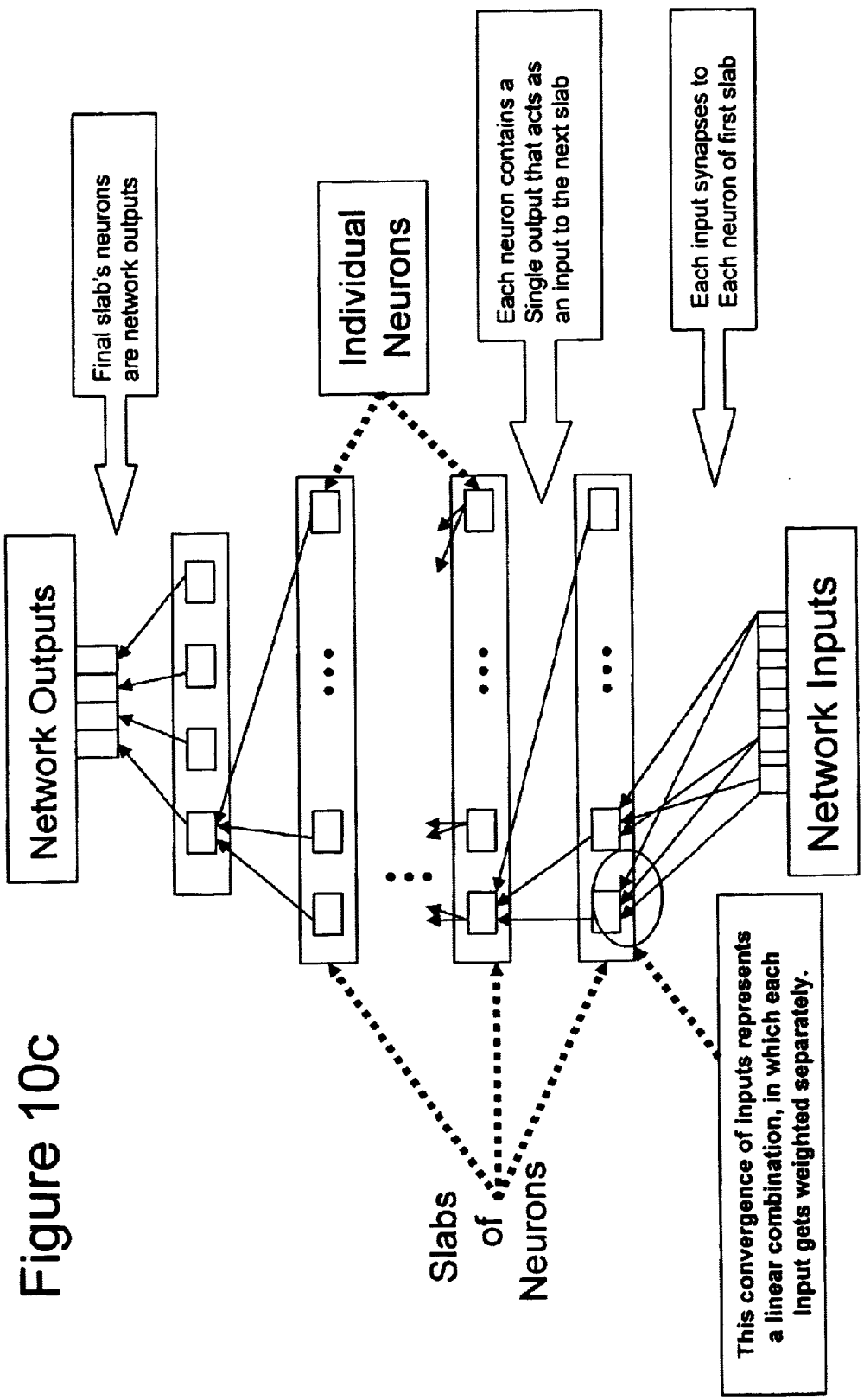
FIG. 10c, which may be compared with FIG. 1, is a mapping neural network diagram of the neural network of the drug dosage estimator in accordance with the present invention.

A block diagram of the construction of a trained single-drug neural network of the drug dosage estimator in accordance with the present invention is shown in FIG. 10a, a block diagram of the construction of the Partitioned Levenberg-Marquardt (pLM) global optimization method of the neural network in FIG. 10b, and a mapping neural network diagram of the neural network of the drug dosage estimator in accordance with the present invention in FIG. 10c. FIG. 10c may be compared with FIG. 1.

Figure 11A:
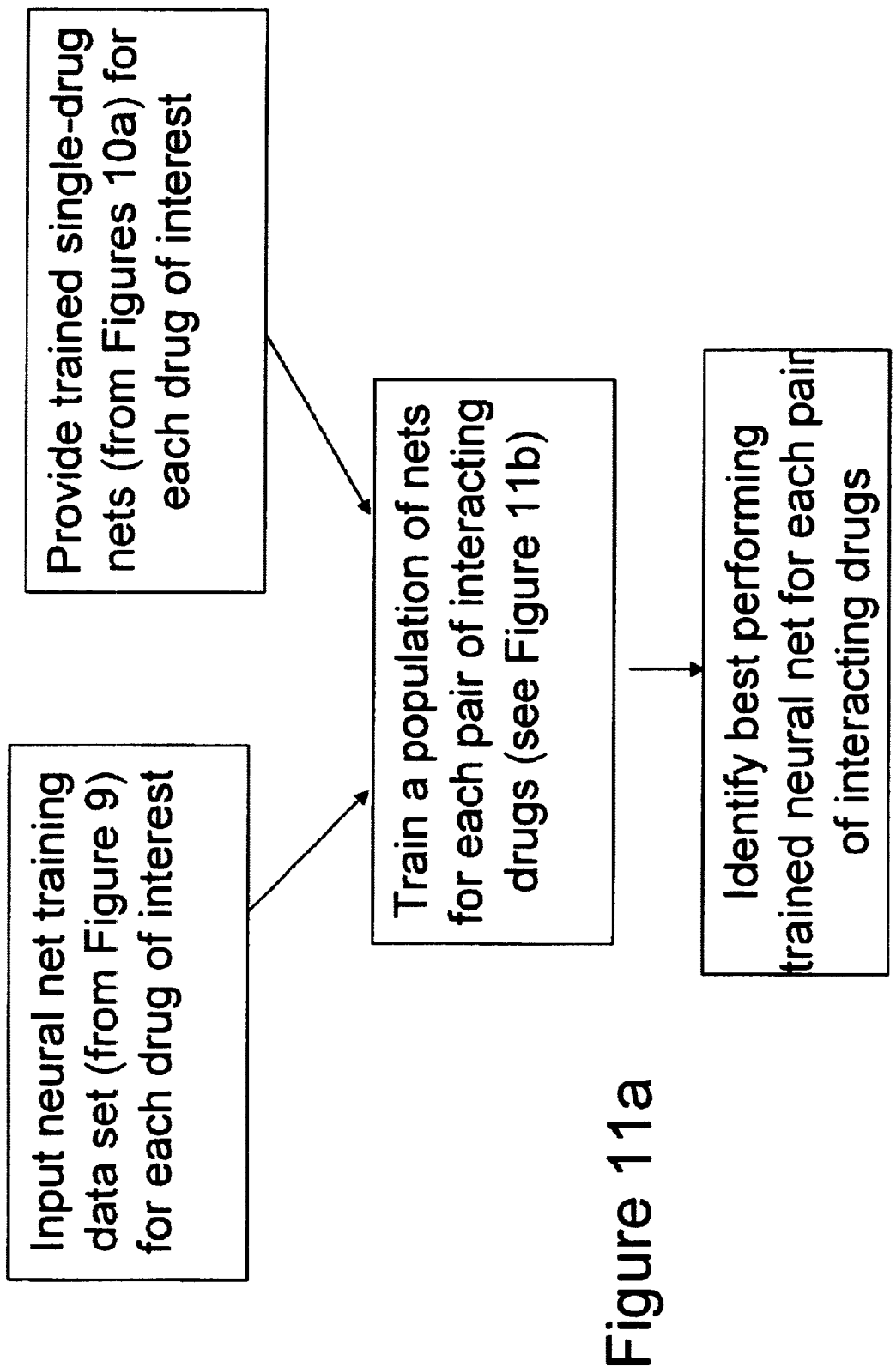
FIG. 11a, which may be compared with FIG. 10a, is a block diagram of the construction of a trained multi-drug neural network of the drug dosage estimator in accordance with the present invention.

A block diagram of the construction of a trained multi-drug neural network of the drug dosage estimator in accordance with the present is shown in FIG. 11a, which may be compared with FIG. 10a.

Figure 11B:
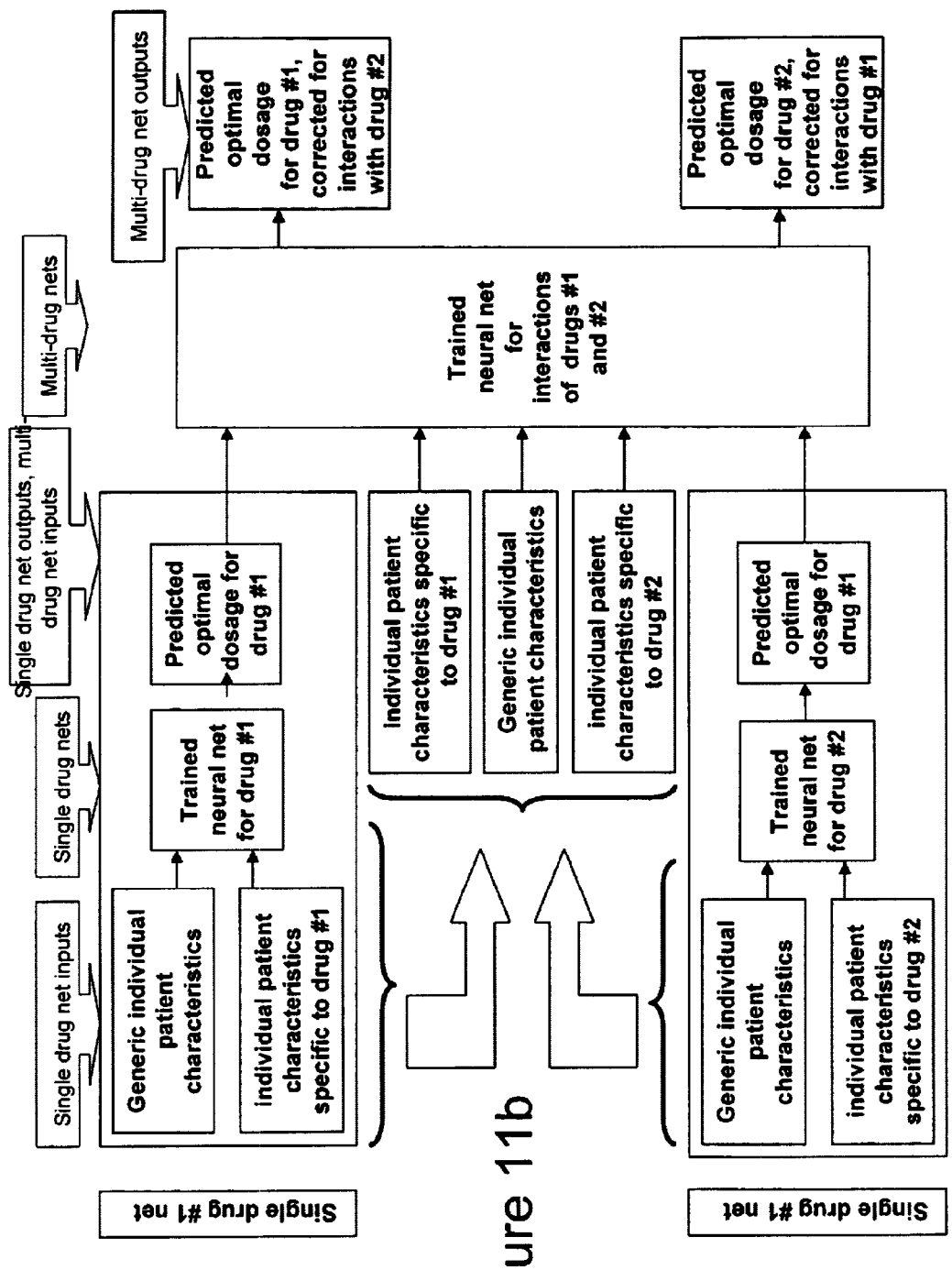
FIG. 11b is an illustration of the method of the present invention for accounting for drug interactions.

An illustration of the method of the present invention for accounting for drug interactions is shown in FIG. 11b.

Figure 11C:
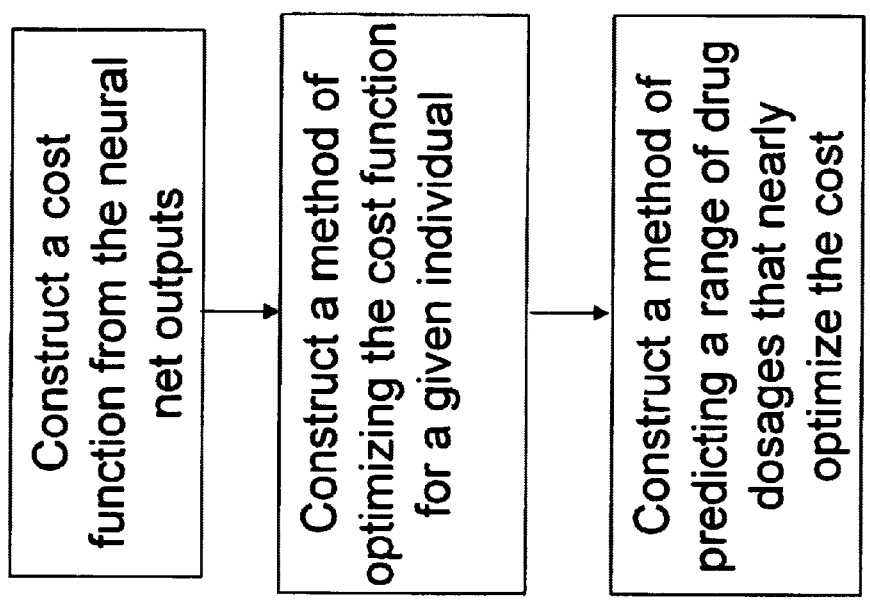
FIG. 11c, which may be compared with FIGS. 10a and 11a, is a block diagram of the construction of a trained multi-drug neural network of the drug dosage estimator in accordance with the present invention when mapping non-optimal drug dosages.

A block diagram of the construction of a trained multi-drug neural network of the drug dosage estimator in accordance with the present invention when mapping non-optimal drug dosages is shown in FIG. 11c, which may be compared with FIGS. 10a and 11a.

Figure 11D:
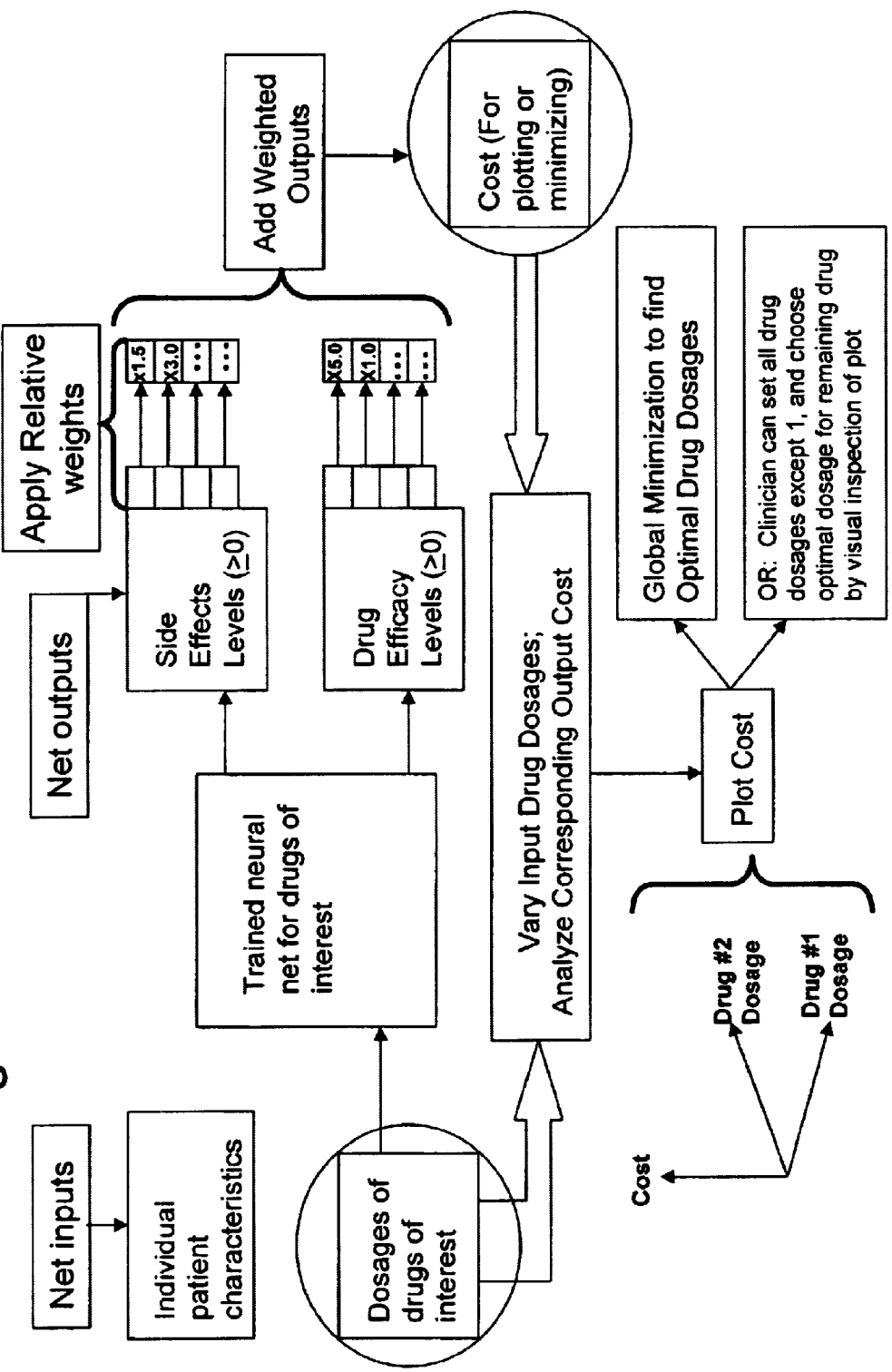
FIG. 11d, which may be compared with FIG. 11b, is an illustration of the method of the present invention for accounting for drug interactions when mapping non-optimal drug dosages.

Finally, an illustration of the method of the present invention for accounting for multiple drug interactions when mapping non-optimal drug dosages is shown in FIG. 11d, which may be compared with FIG. 11b.

Figure 12:
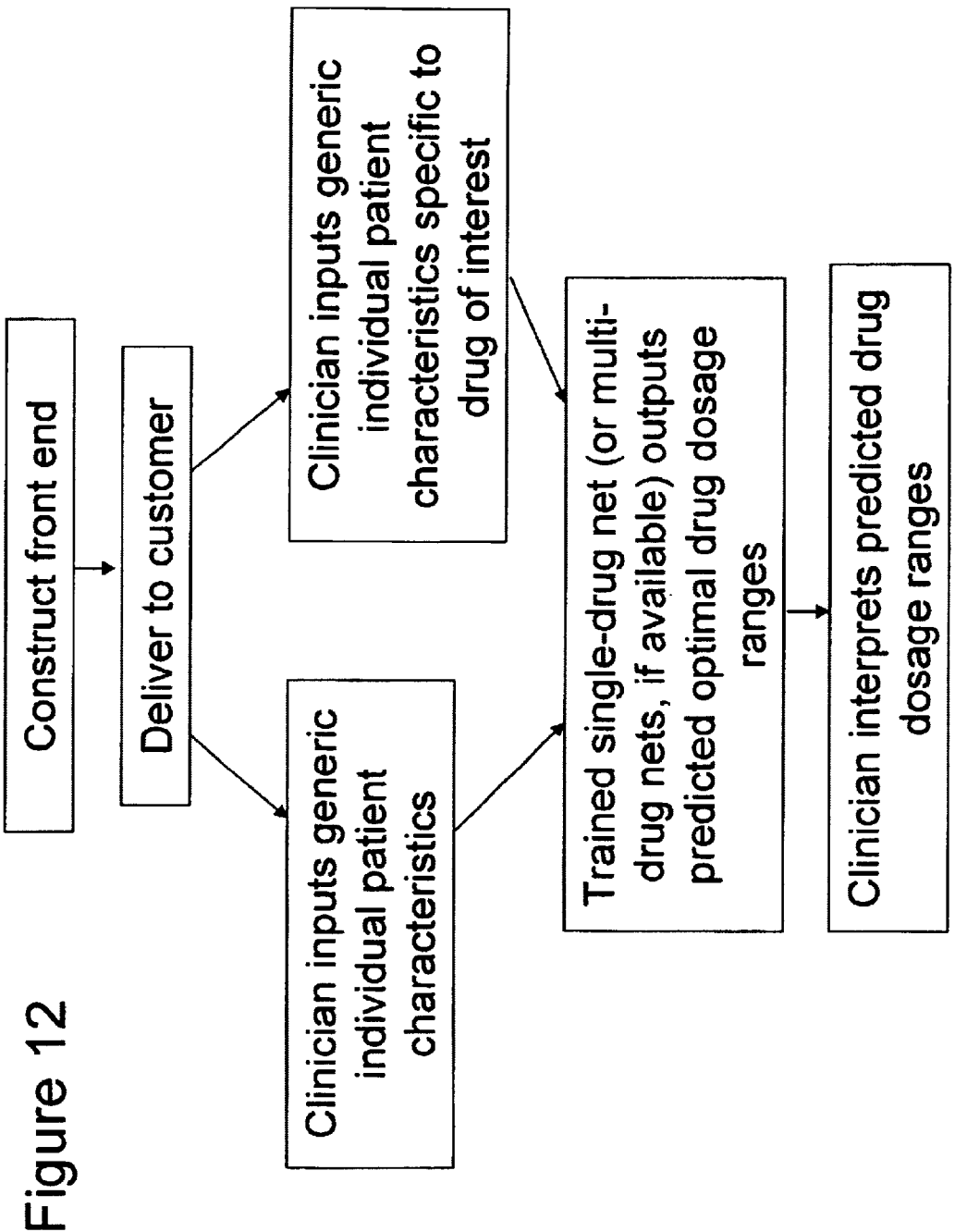
FIG. 12 is a block diagram of a customer's—most normally a physician's—usage of the trained neural network of the drug dosage estimator in accordance with the present invention.

FIG. 12 is a block diagram of a customer's—most normally a physician's—usage of the trained neural network of the drug dosage estimator in accordance with the present invention.

9. Recapitulation

It will by now thus be understood that the inventors have developed and implemented (in C++) a composite neural net training algorithm that incorporates both the Levenberg-Marquardt and simulated annealing global optimization methods. Due to technical difficulties, the Levenberg-Marquardt algorithm is often only implemented for up to three-slab networks. Since the present invention is directed to optimizing neural net architecture with a genetic algorithm, the implementation of which will typically try up to 10 to 20 slabs, an. algorithm supporting arbitrary size networks has been developed. Furthermore, a combination of the two global optimization techniques is used to achieve (i) the speed of the directed error minimization of the Levenberg-Marquardt algorithm, but (ii) the ability of simulated annealing to "jiggle" fitting parameters out of local minima. The result is a fast least squares fitting routine that avoids local minima.

The initial training of the neural net was begun with the use of data gathered from patient records. Tests of the network performance indicate that several small nets are faster and more accurate than one large one. This was noticed by training nets to model a series of monomials (simple polynomials) given only sample random inputs with their corresponding correct outputs (obscured with some noise). When training nets to learn $y=x$ and $y=x^2$, for example, a single net (with 40 neurons in a single hidden layer) charged with outputting both $x$ and $x_2$ took several minutes to several hours on a PC to achieve appropriate chi squared values for the two outputs. On the other hand, two networks of half the size charged with outputting x and $x^2$, respectively, took less time. These observations motivate the decision of the inventors to construct separate, relatively small nets for each (psychotropic) drug of interest, rather than a single, large network for all the drugs of interest and all the diseases of interest.

Optimizing network performance for large nets is ongoing as of the date of this specification. "Large nets" refer to networks with up to about 6 slabs of 100 neurons each, with over 80 inputs and 5 outputs, and with over $10^4$ free parameters. The goal is to experimentally determine good default algorithm parameters for the global optimization techniques. For example, how many rounds of simulated annealing should be performed, and at what numerical temperatures? How many weights should be varied at a time in our piece-wise Levenberg-Marquardt algorithm? Although the inventors are already possessed of such decent defaults as are taught herein, attempts still continue to see if a 10% savings here or there in processing time can be realized.

During the course of. testing the net training software on large nets, the inventors found a way to save still more processing time. As a result, instead of a relatively standard version of the Levenberg-Marquardt (LM) algorithm, the inventors have generally been using what they call the piece-wise Levenberg-Marquardt (pLM) algorithm. The problem that the inventors faced was that their rate-determining step consisted of the solution of a matrix equation contained in the standard LM algorithm. This step required $O(N^2)$ in storage, and took $O(N^3)$ processing time, where N is the number of free parameters contained in the net (often greater than $10_4$ for large nets). To overcome this $N^3$ time barrier and the $N^2$ memory challenge, the inventors attempted optimizing only a fraction of the weights at a time, and repeating the process until each weight had been varied many times. Since only a piece of the network was being varied at one time, the inventors called this the piece-wise LM algorithm. Tests on artificial monomial data (as above) and on finance data indicated that network error was not significantly affected. As a result, it is possible to pLM train large nets that would require well over practical memory constraints (200 Mgs of RAM for a PC) in LM training.

The inventors have also developed and implemented (in the g programming language) a genetic algorithm. Since genetic algorithm runs will some weeks to complete, a graphical user interface was constructed to permit easy monitoring of progress and parameter changes in mid-run.

9.1 Design and Design Methods, Data Collection

It will by now be understood that the patient profile is entered into a standard spreadsheet. Depending upon the number of relevant independent variables for a given drug, the minimum number of cases required to train the neural network is on the order of 500 to 2,000, and the number of cases used is more commonly of the order of 10,000. The neural net specialist will then translate the data to a format appropriate for input to a neural network. This will consist of reformatting the spreadsheet documents using the Perl scripting language and reading it into a C++ subroutine of the neural net software.

9.2 Computer Languages

The front-end was programmed in the G programming language associated with the LabView development environment. This has the advantage of being a platform independent windowing language, i.e., its use is not confined to the use of a particular operating system. Another advantage is that it is amenable to use over the Internet; our software could be accessed through its graphical user interface from any machine equipped with a browser.

The neural net training software was programmed in the C++ programming language. This is an industry-standard, object-oriented language with limited text processing tools and no portable windowing capabilities. Its advantage is that it allows the programmer to take full advantage of the machine for calculations; the same algorithms implemented in G, for example, could take 10 to 100 times longer.

While interaction with the Research Groups and any main patient Database Group to determine the best mode of data storage and transfer is important, the inventors intend that the preprocessing of the spreadsheet data files is performed with the Perl scripting language. This is a free language optimized for text processing, and most automatically generated web pages are constructed with Perl scripts. The advantage here is much greater functionality than spreadsheets, allowing seemingly trivial formatting changes that are not generally supported by spreadsheets to be done easily.

9.3 Data Analysis

It will by now be understood that the neural net analysts train the networks to "memorize" the optimal drug dosage as clinically determined. A separate neural net will be constructed for each psychotropic drug of interest. Several separate nets are more efficient than a single large one because the less information an individual network is expected to learn, the better its performance. As described above, an individual neural network consists of inputs and outputs and is trained by correct examples of input/output pairs. In this case, the input/output pairs will be obtained as follows. The inputs will consist primarily of binary demographic variables. The outputs will consist of the optimal drug dosage as clinically determined.

The analysts will use. neural network training routines within a genetic algorithm. The genetic algorithm selects a variety of network architectures for the training routines to test. The training routines include a combination of the Levenberg-Marquardt and simulated annealing neural net training algorithms to increase speed of training compared to traditional neural net training techniques. This increase in speed enables us to train on personal computers rather than supercomputers.

The front-end will be programmed in g, which is a platform independent graphical language associated with the Labview development environment. As such, it is not confined to use of particular operating systems. It is also amenable to use over the Web, which allows the program to be accessed from any machine equipped with a browser. The front-end is the graphical interface that the clinician will use. It will consist of input fields for entering of individual characteristics and the drug(s) of interest, and output fields for optimal dosage ranges for those drugs.

9.4 Interpretation

It will by now thus be understood that, unlike most neural network applications in current use, the implementation of the present invention actually produces an estimate of the uncertainty of the outputs. Furthermore, this estimate of the error is more precise than that produced by standard statistical techniques, which analyze the output based upon the assumption of a global average. Since these traditional techniques ignore individual differences, the approximation has a larger standard deviation than one that does account for such differences. Such an accounting of multiple independent variables as we propose with a neural net should produce a smaller variance due to a more precise fitting of the data. In this way, we will calculate a variance estimate for each drug that will be smaller than the crude population average routinely used. This smaller variance will complement the dosage prediction specific to an individual. The significance to the field worker is that she will obtain a more accurate and more precise optimal dosage prediction than an average over the entire training data set.

9.5 Potential Difficulties and Proposed Alternatives

It should by now be understood that the training of substantial networks with a genetic algorithm can require weeks of supercomputer time at extreme cost. To speed the training process and avoid the necessity of using a supercomputer, the inventors have implemented several innovations to the training process. These include the primary innovations of the use of Levenberg-Marquardt and simulated annealing global optimization techniques, which permit training of the large networks on a personal computer. As indicated by the studies of the inventors, additional time savings as well as improved accuracy can be obtained by constructing an aggregate of smaller nets specific to each drug rather than a single large net that includes all of the drugs and disorders of interest.

Due to the variety of variables considered, the training data set cannot contain examples of all possible combinations of inputs. For example, for a given disorder, the testing population may not contain a participant who is a Hispanic female and is in the specific age range of 20 to 25 years old, but the field worker may encounter such a case. However, a neural network can extrapolate this information from prior "learning" based upon training conducted with related test cases, such as dosages for male Hispanics of similar age and Hispanic females of different age ranges.

As previously described, it is generally believed that one cannot perform hypothesis testing with neural nets. A potential difficulty with our technique is that it is only useful to the clinician and is not relevant to researchers. However, the method of the present invention will by now be realized to permit performance of such testing as permits the trained neural networks of the present invention to be directly useful in conducting hypothesis-driven research.

9.6 A Typical Project

It will by now be understood that a typical neural network implementation and use in accordance with the present invention typically occurs in three general phases, although there will most likely be some overlap among them.

Phase 1 is to write the neural network software. A mapping neural net using a backpropagation architecture with global optimization routines is used, and the network architecture is preferably chosen by a genetic algorithm. Although mapping neural net routines are already publicly available, support for global optimization is rare (as it is the state of the art), and simultaneous support for either incomplete data sets or for a genetic algorithm is not available.

Phase 2 will be the ongoing receipt of data from a medical research groups and/or a main historical medical database archivist. Depending upon the number of relevant independent variables, the number of cases required to train the neural network is on the order of a minimum of 500 to 2,000, and more commonly 10,000. This Phase 2 also includes the writing of routines to interface the data collection efforts with the neural nets and the writing of a front end to interface the neural nets with the end user.

Phase 3 comprises training the network using the data collected. The program is tested by clinicians to determine its validity in predicting effective dosages. This most normally occurs in several trials as it may be necessary to fine-tune iterations of the output. The immediate goal is to exercise the present invention for ever more members of a specific group of drugs, e.g., antidepressants or antipsychotics. In the longer term, the present invention is intend to be used to encompass all groups of psychotropic medications, and still other drugs.

9.7 Genetic Algorithms

It will by now also be known to the reader that genetic algorithms (GA's) were developed by John Holland in the 1970's and are based on a Darwinian-type survival-of-the-fittest strategy with sexual reproduction, whereby stronger individuals in the population have a higher chance of creating offspring. See van Rooij, A. J. F. Jain, L. C. & Johnson R. P. (1996); *Neural network training using genetic algorithms;* World Scientific Publishing Co., Singapore.

Each individual in the population represents a potential solution to the problem that is to be solved. The individuals are represented in the genetic algorithm by means of a linear string similar to the way genetic information is coded in organisms as chromosomes. In GA terminology, the members of a population are therefore referred to as chromosomes. Chromosomes are made up of a set of genes, and in the traditional case of binary strings these genes are just bits.

It will also be understood that the definitions of the basic terms in a genetic algorithm are given below:

A phenotype is the potential solution to the problem.

A chromosome is the representation of the phenotype in a form that can be used by the genetic algorithm (generally as a linear string).

A genotype is the set of parameters encoded in the chromosome.

A gene is the non-changeable pieces of data from which a chromosome is made up.

An alphabet is the set of values a gene can take on.

A population is the collection of chromosomes that evolves from generation to generation.

A generation is a single pass from the present population to the next one.

Fitness is the measure of the performance of an individual on the actual problem.

Evaluation is the translation of the genotype into the phenotype and the calculation of its fitness.

Using this terminology, the following steps describe the operation of the standard genetic algorithm.

First, randomly generate an initial population of chromosomes.

Second, compute the fitness of every member of the current population.

Third, make an intermediate population by extracting members out of the current population by means of the reproduction operator.

Fourth, generate the new population by applying the genetic operators (crossover, mutation) to this intermediate population.

Fifth, if there is a member of the current population that satisfies the problem requirements then stop, otherwise return to the second step.

The reproduction (or selection) operator that is most commonly used is the roulette wheel method, where members of a population are extracted using a probabilistic Monte Carlo procedure based on their average fitness. For example, a chromosome with a fitness of 20% of the total fitness of a population will, on an average, make up 20% of the intermediate generation. Apart from the roulette wheel method many other selection schemes are possible.

The heuristics of GA's are mainly based on reproduction and on the crossover operator, and only on a very small scale on the mutation operator. The crossover operator exchanges parts of the chromosomes (strings) of two randomly chosen members in the intermediate population and the newly created chromosomes are placed into the new population. Sometimes instead of two, only one newly created chromosome is put into the new population; the other one is discarded. The mutation operator works only on a single chromosome and randomly alters some part of the representation string. Both operators (and sometimes more) are applied with a certain probability. FIG. 1 shows the flowchart of the standard genetic algorithm.

The stopping criterion is usually set to that point in time when an individual that gives an adequate solution to the problem has been found or simply when a set number of generations has been run. It can also be set equal to the point where the population has converged to a single solution. A gene is said to have converged when 95% of the population of chromosomes share the same value of that gene. Ideally, the GA will converge to the optimal solution; sometimes however a premature convergence to a sub-optimal solution is observed.

9.8 Comparison to Biological Systems

In biological systems from which the genetic algorithm terminology originates, a genotype, or the total genetic package, is a structure made up of several chromosomes. The phenotype is the actual organism formed by the interaction of the genotype with its environment. In genetic algorithms however, an individual is usually represented by a single chromosome and therefore the chromosome and the genotype are one and the same.

A GA is sometimes compared to a Darwin model of evolution. The main overall difference between the two systems lies in their goals, (or rather the lack of one in Darwinian evolutionary theory). While in evolutionary computation the goal almost always is the optimization of some kind of fixed problem, this does not necessarily seem to be the case for biological evolutionary systems. Still, the success of evolutionary computation as a function optimizer, as reported on a wide variety of problems and in some parts supported by theoretical foundation, indicates that many features of Darwinism lend themselves very well for this purpose. Table 1 shows differences between the two models.

The aim of the genetic algorithm is to find an individual with a maximum fitness by means of a stochastic global search of the solution space.

9.9. General Embodiment of the Invention as Seen in Use by, Inter Alia, a Physician Prescribing Drugs Finally, it will be understood that the present invention is thus embodied in a method and system to quickly and precisely recommend a drug dosage for a particular patient. This objective is accomplished by providing a computerized, patient-specific, drug dosage estimator for use by, inter alia, a physician prescribing drugs.

The computerized system includes an input device which inputs post-training patient information input data about the particular patient. An electronic processing unit or units receive the patient information input data. The processing unit generates a plurality of drug of interest dosage values. The processing unit extrapolates, non-linearly, from an example data group, a plurality of patient information data outputs. Each extrapolated output is extrapolated to fit both the patient information data input and a corresponding drug of interest dosage value. The processing unit determines which of the drug dosages of interest results in an optimal extrapolated outputs for the patient. An electronic display interfaced with the processing unit displays the optimal extrapolated patient information data output as a recommended drug dosage to be taken by the patient.

The post-training patient information data input can include a plurality of patient characteristic values. The patient characteristic values can include age values, sex values, ethnicity values, and health characteristic values such as blood pressure values, weight values and glucose level values. The corresponding drug of interest dosage values are generated by the CPU. The example data group corresponds to a series of input data sets. Each data set includes categories of information classified as example patient information input data and corresponding example patient information output data.

10. Extension of Drug Dosage Methods of the Present Invention to Diet and/or Exercise Management The drug dosage estimation methodologies of the present invention can be applied to diet and exercise management. This use consists of treating various types of food or exercise as the drug of interest and clinically measurable quantities such as blood pressure and cholesterol level as the outputs. Note that the method of the present invention applies equally well to any quantity that a patient takes in measured doses, even if not a chemical. For example, exercise is such a quantity. The predictions thus need not refer to diet. For example, a patient may wonder how much he or she can lower his or her blood pressure by a combination of cutting back on their cigarette smoking and by walking a few hours a week. The same methods used by the present invention to predict the effects of drug dosages also apply in this case, with the amounts of smoking and of walking considered to be the dosages of two drugs that the patient is taking, and with blood pressure the side effect.

Figure 13:
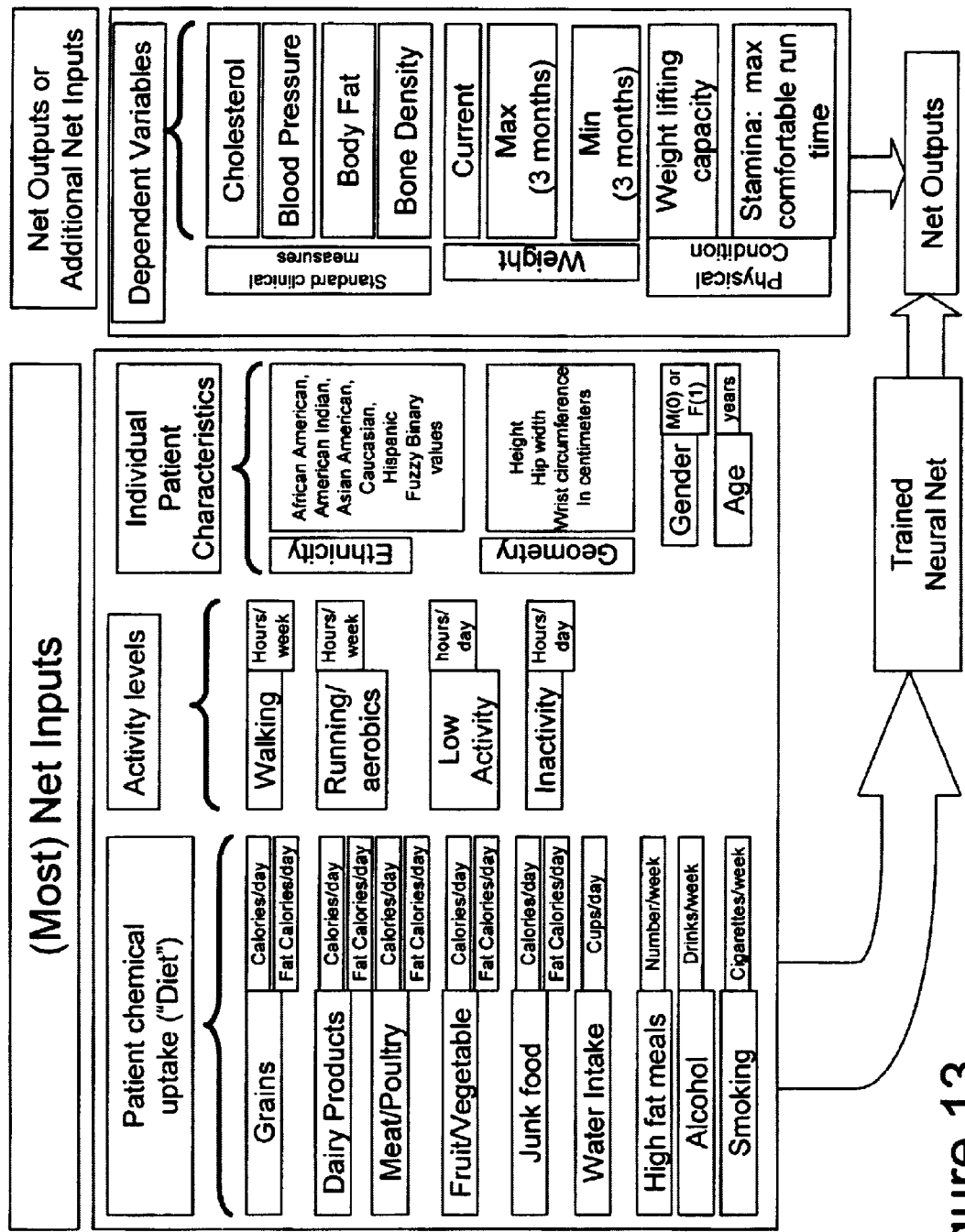
FIG. 13 is a block diagram of the extension of the trained neural network method of the of present invention to dietary management, with input and output data appropriate to this application being in particular shown.

The types of inputs and outputs that would be used in such an application of the invention are illustrated in FIG. 13. The inputs can be categorized as pertaining to diet, activity levels, and individual patient characteristics. The outputs can be drawn from a set of dependent variables listed in the diagram and organized into three additional categories: standard clinical measures (such as blood pressure), weight measures, and physical condition measures. Those quantities not being used as outputs may be used as inputs or may be ignored. The lists here may be impractically large, as sufficient data sets may not be available for training. Many of the sets of variables can be simplified to reduce the total number of variables. It should be noted that the maximum and minimum weights referred to in the dependent variables refer to the past (the past 3 months, for example) if these are used as inputs, and to the future (expected values for the next 3 months, for example) if they are used as outputs.

The steps involved in training neural nets in accordance with the invention in this context of diet management are illustrated in FIG. 13. It should be noted that a separate neural net needs to be trained for each distinct choice of variables to be used for the inputs and outputs.

Figure 14:
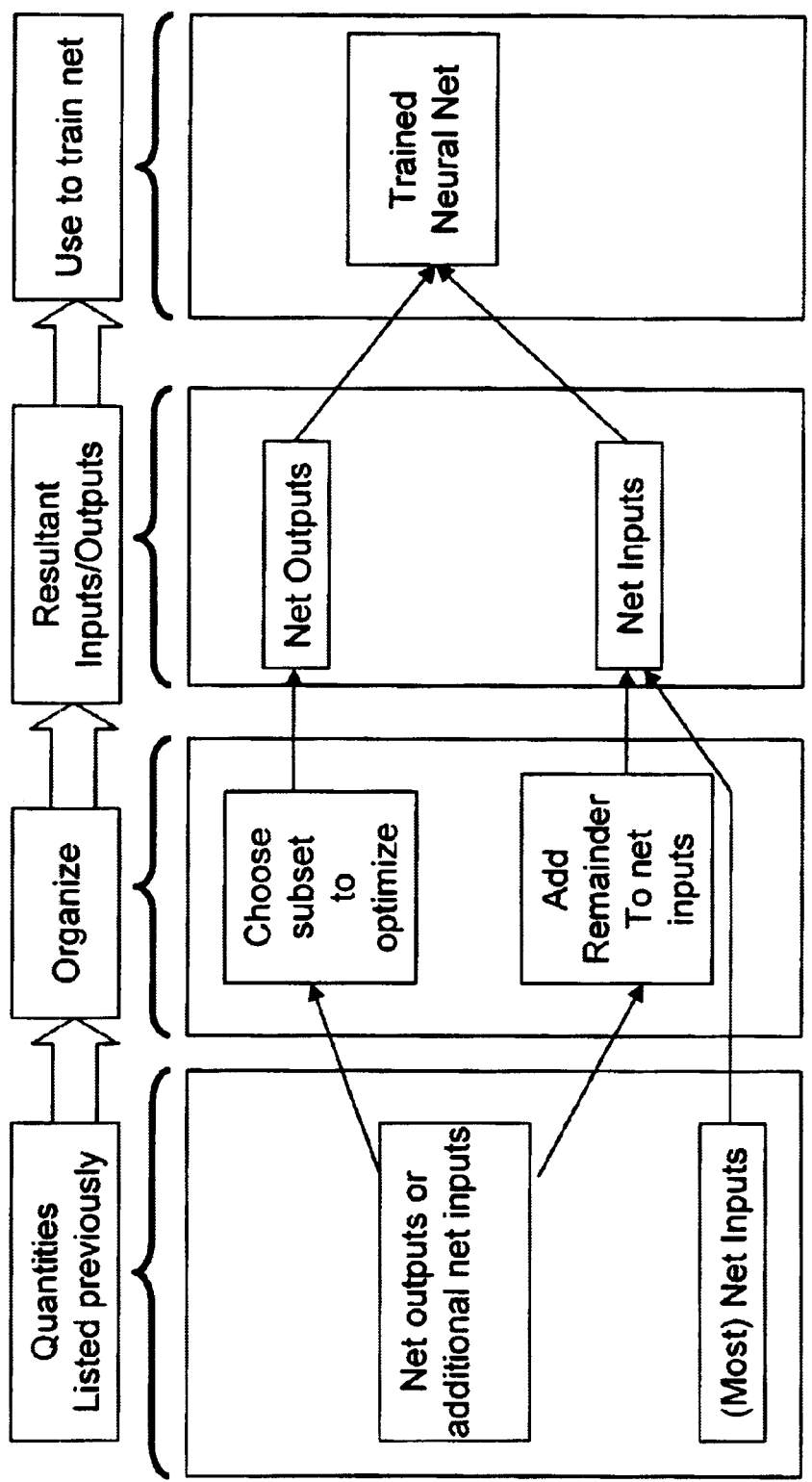
FIG. 14 is a block diagram of the steps in training a neural network in accordance with the present invention to perform dietary management.
Figure 15:
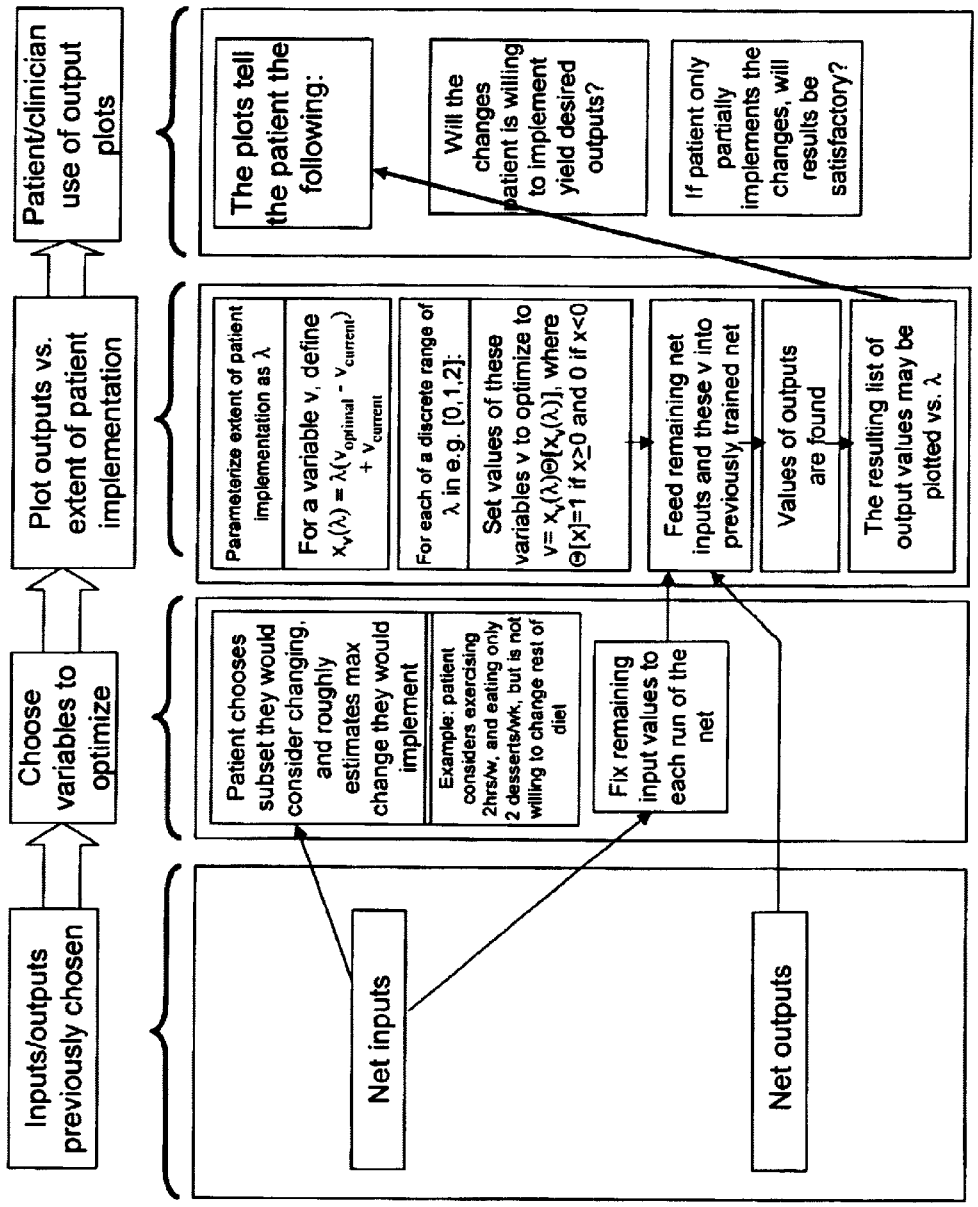
FIG. 15 is a block diagram of the steps of using a neural network in accordance with the present invention to perform dietary management.

Finally, the steps involved in using trained neural nets in accordance with the present invention for diet management are illustrated in FIG. 14. The method is intrinsically amenable to a high amount of patient interaction. The patient decides which of the input variables for which they personally believe they may be willing to modify their behavior. For example, a patient may be willing to limit their number of desserts per week to 2, and they may be willing to run a couple of hours a week, but they're not willing to start running or to eat healthier foods. FIG. 15 illustrates how the technique of the present invention can quantitatively incorporate such nebulous patient preferences spanning multiple variables. Essentially, a neural net that has previously been trained is used to determine the probable results of the patient's hypothetical implementation of their proposed changes. The present invention goes further, however, and even permits drawing a plot illustrating for the patient what will happen if the patient doesn't completely incorporate all the changes they thought they could. So if they thought the patient intended to run for 2 hours a week but only ran for an average of 45 minutes, they would know how much to expect their blood pressure or weight to change.

11. Conclusion

In accordance with the preceding explanation, variations and adaptations of the neural network drug dosage estimation method and system in accordance with the present invention will suggest themselves to a practitioner of the computer system and computer software design arts.

For example, additional uses of the same techniques of the present invention are possible.

For example, the techniques of the present invention may be used to estimate optimal body weight. Different classes of foods or exercises may be treated as drugs, and "side effects" such as cholesterol levels, blood pressure, etc. mapped out as a function of intake of various foods or amount of exercise. This could be used to determine empirically healthy diet and exercise regimens. This could also yield optimal weight ranges for individuals that are more realistic than the standard tables based only on age, height, and gender.

For example, the techniques of the present invention may be used to in formulating strategy for the control of epidemics in the face of limited resources including drugs. Scarce vaccine or antibody resources could prove entirely inadequate to defend a population against an outbreak of an existing disease, such as might be due to plague or war, if standard dosages are used. By empirically determining the actual amount of these scarce quantities that are required for protection within a given amount of time, wasteful use could be eliminated and smaller dosages could be strategically implemented in exchange for longer time lags to protection. Careful management of scarce resources could then be used to protect an entire population.

In accordance with these and other possible variations and adaptations of the present invention, the scope of the invention should be determined in accordance with the following claims, only, and not solely in accordance with that embodiment within which the invention has been taught.

What is claimed is:

1. A method of predicting an optimal dosage of a particular drug for a particular patient comprising:
    receiving a database of the characteristics and optimal drug dosage of the particular drug for a multiplicity of patients;
    receiving data on the characteristics of a particular patient corresponding at least in part to those characteristics that are within the database; and
    interpolating in a computer neural network the optimal drug dosage for the particular patient in consideration of the characteristics and optimal drug dosage database.

2. The method according to claim 1 wherein the interpolating is in a computer neural network optimized to relate optimal drug dosage to the patient characteristics of the database.

3. A computerized method of predicting an optimal dosage of a particular drug for a Particular Patient in consideration of previously determined optimal dosages of the drug for members of a patient population, the computerized optimal drug dosage prediction method comprising:
    programming a plurality of neural networks each having an architecture of one or more slabs collectively relating input data to output data,
    wherein said input data includes at least a selected three (3) of a person's traits drawn from at least two (2) of the following three (3) groups consisting of
        Group 1 overt indications of
            (1a) age,
            (1b) gender,
            (1c) race,
            (1d) ethnicity,
            (1e) diet type,
            (1f) height,
            (1g) weight, and
            (1h) body surface area,
        Group 2 medical diagnostic indications of
            (2a) blood pressure,
            (2b) use of a drug other than the particular drug at the same time as use of the particular drug,
            (2c) fitness,
            (2d) peptide levels, and
            (2e) genetic predisposition to a particular disease, and
        Group 3 pharmacological indications of
            (3a) pharmacokinetic parameters,
            (3b) pharmacodynamic parameters, and
    wherein said output data includes clinically-determined optimal drug dosage for the same person;
    training each of the plurality of programmed neural networks with a training data set drawn from a multiplicity of historical medical records of a multiplicity of persons historically administered the particular drug, the records relating the selected input data to the output data;
    selecting one of plurality of neural networks that performs best on the training data set to be a selected trained neural network;
    using the selected trained neural network to predict an optimal dosage of the particular drug for the Particular Patient, the using transpiring by inputting the selected input data, which input data is at least a selected three (3) of The Particular Patient's traits drawn from at least two (2) of the three (3) groups consisting of Group 1 overt indications and Group 2 medical diagnostic indications and Group 3 pharmacological indications, to ascertain as (2) output of the trained neural network the output data, which output data is the predicted optimal dosage for the Particular Patient.

4. The computerized drug dosage prediction method according to claim 3
    wherein the architectures of the plurality of neural networks are established by a same human who does the programming of the neural network, one human thus acting as both neural network architect and neural network programmer.

5. The computerized drug dosage prediction method according to claim 3 wherein the selecting comprises:
  choosing one of the plurality of neural networks by a genetic algorithm, the genetic algorithm acting to select the one of the plurality of neural networks that performs best on the training data set; and
  wherein the training of each of the plurality of neural architectures permits, along with the choosing, not only a selection a single one of the plurality of neural networks that performs best on the training data set, but the training of this selected one of the plurality of neural networks to optimally relate the input data to the output data.

6. The computerized drug dosage prediction method according to claim 3 extended and expanded to account for interaction between at least two, a first and a second, drugs taken concurrently by the Particular Patient, the extended method comprising:
  performing the programming, the training, the selecting and the using in respect of a first drug to predict in a first selected trained neural network an optimal dosage of the first drug for the Particular Patient;
  performing the programming, the training, the selecting and the using in respect of a second drug to predict in a second selected trained neural network an optimal dosage of the second drug for the Particular Patient;
  programming a plurality of drug interaction neural networks each having an architecture of one or more slabs collectively relating (3) second data inputs drawn from the group consisting of
    (3a) the first drug optimal dosage;
    (3b) the second drug optimal dosage; and
    (3c) the first data inputs for the first trained neural network, and
    (3d) the first data inputs for the second trained neural network, and having as an (4) output
    (4a) the clinically-determined optimal drug dosage for the first drug, and
    (4b) the clinically-determined optimal drug dosage for the second drug; and
  training each of the plurality of drug interaction neural networks with a training data set drawn from a multiplicity of historical medical records of a multiplicity of persons historically administered the two particular drugs, these records relating the input data to the output data, to produce a plurality of trained drug interaction neural networks;
  selecting a one of plurality of trained drug interaction neural networks that performs best on the training data set to be a selected trained drug interaction neural network;
  using the selected trained drug interaction neural network to predict the optimal dosage of both the first and the second drug for the Particular Patient;
  wherein each drug's optimal dosage is in respect of the other drug's optimal dosage.

7. The computerized drug dosage prediction method according to claim 6 wherein the selecting comprises:
  choosing a one of the plurality of drug interaction neural networks by a genetic algorithm, the genetic algorithm acting to select the one of the plurality of drug interaction neural networks that performs best on the training data set;
  wherein the training of the drug interaction neural network is of each of the plurality of neural network architectures to produce a single optimal drug interaction neural network architecture as well as to train this single optimal drug interaction neural network architecture, when identified, to relate the optimal dosage of a first drug in respect of a patient's simultaneous usage of a second drug.

8. A computerized method of predicting an optimal dosage of a particular drug for a Particular Patient, the method comprising:
  programming a neural net that relates drug dosage to drug efficacy and to drug side effects;
  training the neural network in consideration of both (i) efficacy and (ii) side effect measures from usages of the drug at determined dosages on members of a population to produce a trained neural network;
  using the trained neural network to predict a drug dosage for an individual patient that (i) delivers adequate measures of efficacy while (ii) minimizing adverse side effects.

9. The computerized method of predicting an optimal dosage of a particular drug according to claim 8 wherein the using comprises:
  repeatedly exercising the neural network in respect of various drug dosages to assess the (i) measures of efficacy and (ii) adverse side effects in respect of each dosage, ultimately selecting the drug dosage for the Particular Patient that (i) delivers the adequate measures of efficacy while (ii) minimizing the adverse side effects.

10. A method of creating a neural network both (i) optimized and (ii) trained to predict the optimal dosage of a particular drug for a particular patient, the optimal trained neural network creation method comprising:
  acquiring neural network training data as
    raw data from patient medical records, the raw data being in the form of recorded patient responses to recorded patient drug dosages in respect of patient characteristics,
    the patient medical records being categorized for relevance, so as to produce
    relevant categorized patient drug response data in respect of patient characteristics;
  designing and programming a plurality of neural networks each of which may suitably operate upon the neural network training data by
    programming a framework for each of the plurality of neural networks;
    programming a genetic algorithm for framework for each of the plurality of neural networks, and
    interfacing the programmed framework with the programmed genetic algorithm; then
  training each of the plurality of neural networks with the neural network training data until, by operation of the genetic algorithm, a single optimal, trained neural network is selected;
  wherein the selected single optimal, trained neural network is then both (i) optimized, meaning selected as the best of many, and (ii) trained, meaning proven on data of relevance, to predict the optimal dosage of a particular drug for a particular patient.

11. The method according to claim 10 wherein the training is by the back propagation method.

12. The method according to claim 10 wherein the training is by the Levenberg-Marquardt optimization method.

13. An optimal, trained, neural network created by the method of claim 10.

14. A computerized method of predicting an optimal dosage of a particular drug for a Particular Patient, the method comprising:

performing in a recurring, iterative, looped process each of the steps of
(1) programming a neural network that relates drug dosage to drug efficacy and to drug side effects, and
(2) training the neural network in consideration of a historical data set of both efficacy and side effect measures from usages of the drug at determined dosages on members of a population,
wherein the (1) programming transpires in consideration of the results of the (ii) training,
so long as, and until, an optimally programmed and trained neural network adequately accurately predicts both drug efficacy and drug side effects relative to drug dosage; then exercising the optimally programmed and trained neural network on a range of drug dosages in order to examine the predicted sensitivity of both drug efficacy and drug side effects relative to the range of drug dosages;

wherein a physician prescribing the drug can, by observation of the results of the exercising, make a better informed decision as to what patient dosages of the drug are likely to deliver both tolerable efficacy and tolerable side effects.

15. A computerized method of predicting the effect of one or both of dietary items consumed or exercises performed on measured physiological characteristics of a Particular Patient, the method comprising:

programming a neural net that relates any of selected dietary items consumed and exercises performed on measured physiological characteristics of patients as might be expected to be affected by the selected dietary items and exercises;

training the neural network in consideration of historical data on the impact of the dietary items consumed and exercises performed on the physiological characteristics evidenced by members of a population, therein to produce a trained neural network;

using the trained neural network to predict the change in physiological characteristics to be anticipated for an individual Particular Patient who consumes any of the selected dietary items and/or performs any of the selected exercises.

16. The computerized method of predicting the effect of one or both of dietary items consumed or exercises performed on measured physiological characteristics of a Particular Patient according to claim 15 wherein the using comprises:

repeatedly exercising the neural network in respect of various selected dietary items consumed and/or selected exercises performed to assess the (i) measures of efficacy and (ii) adverse side effects in respect of each selected dietary item consumed and/or selected exercise performed, ultimately selecting dietary items and/or exercises the Particular Patient that (i) delivers adequate measures of efficacy while (ii) maximizing acceptability and suitability to the Particular Patient's preferences and conduct.

* * * * *